United States Patent
Hilfiker et al.

(10) Patent No.: US 6,441,902 B1
(45) Date of Patent: Aug. 27, 2002

(54) METHOD FOR EVALUATING SAMPLE SYSTEM ANISOTROPIC REFRACTIVE INDICES AND ORIENTATIONS THEREOF IN MULTIPLE DIMENSIONS

(75) Inventors: James N. Hilfiker; Corey L. Bungay; Craig M. Herzinger, all of Lincoln, NE (US)

(73) Assignee: J. A. Woollam Co. Inc., Lincoln, NE (US)

( * ) Notice: Subject to any disclaimer, the term of this patent is extended or adjusted under 35 U.S.C. 154(b) by 0 days.

(21) Appl. No.: 09/474,318

(22) Filed: Dec. 29, 1999

Related U.S. Application Data

(60) Provisional application No. 60/126,552, filed on Mar. 26, 1999.

(51) Int. Cl.[7] .............................. G01J 4/00; H01J 4/14
(52) U.S. Cl. ....................... 356/369; 250/225
(58) Field of Search ................................ 356/364, 365, 356/369; 250/225

(56) References Cited

U.S. PATENT DOCUMENTS

| | | | |
|---|---|---|---|
| 4,053,232 A | 10/1977 | Dill et al. | 356/118 |
| 4,668,086 A | 5/1987 | Redner | 356/33 |
| 5,329,357 A | 7/1994 | Bernoux et al. | 356/369 |
| 5,373,359 A | 12/1994 | Woollam et al. | 356/328 |
| 5,504,582 A | 4/1996 | Johs et al. | 356/369 |
| 5,521,706 A | 5/1996 | Green et al. | 356/369 |
| 5,581,350 A | 12/1996 | Chen et al. | 356/369 |
| 5,596,406 A | 1/1997 | Rosencwaig et al. | 356/327 |
| 5,666,201 A | 9/1997 | Johs et al. | 356/369 |
| 5,757,494 A | 5/1998 | Green et al. | 356/369 |
| 5,805,285 A | 9/1998 | Johs et al. | 356/369 |
| 5,835,222 A | 11/1998 | Herzinger | 356/369 |
| 5,872,630 A | 2/1999 | Johs et al. | 356/369 |

*Primary Examiner*—Zandra Smith
(74) *Attorney, Agent, or Firm*—James D. Welch

(57) ABSTRACT

Disclosed is a method of evaluating sample system anisotropic refractive indices, and orientations thereof with respect to an alignment surface, in multiple dimensions. The preferred method involves a sequence of steps which allows overcoming mathematical model parameter correlation during mathematical regression parameter evaluation, even though individually, steps of the present invention method wherein anisotropic refractive indices, or differences therebetween, are evaluated, require that only a relatively simple one dimensional data set be acquired.

27 Claims, 8 Drawing Sheets

1.
Determining the precise orientation of a third ($n_z$) essentially orthogonal index of refraction which projects essentially perpendicular to an alignment surface of a sample system, said alignment surface being characterized by two essentially in-plane, ($n_x$) and ($n_y$), indices of refraction.

2.
Causing a spectroscopic beam of electromagnetic radiation originating from a source of a beam of electromagnetic radiation, (which spectroscopic beam of electromagnetic radiation is preferably essentially linearly polarized and is comprised of a plurality of wavelengths for which said sample system is essentially transparent), to approach said alignment surface of said sample system along a locus which is essentially co-incident with the orientation of the third ($n_z$) orthogonal index of refraction, at least partially transmit through said sample system and enter a transmission detector to the end that a one-dimensional data set as a function of wavelength is acquired; and applying said computational means which is programmed with a mathematical model for said sample system to the end that a value for the difference between the in-plane ($\Delta n_{xy}$) indices of refraction and the Euler angle orientations of said essentially in-plane orthogonal ($n_x$) ($n_y$) indices of refraction are determined.

3.
Causing a beam of electromagnetic radiation originating from said source of a beam of electromagnetic radiation, (which beam of electromagnetic radiation is preferably essentially linearly polarized and is comprised of at least one wavelength), to approach said alignment surface of said sample system along a plurality of near normal angles-of-incidence to said sample system alignment surface, interact with said sample system and enter said transmission and/or reflection detector to the end that a one dimensional data set as a function of angle-of-incidence is acquired; and applying said computational means which is programmed with a mathematical model for said sample system to the end that a value for the difference between at least one out-of-plane combination of indices of refraction selected from the group consisting of ($\Delta n_{xz}$), and ($\Delta n_{yz}$) is determined.

FIG. 3

4.
Causing a beam of electromagnetic radiation originating from said source of a beam of electromagnetic radiation, (which beam of electromagnetic radiation is preferably essentially linearly polarized and is comprised of at least one wavelength), to approach said alignment surface of said sample system along a plurality of angles-of-incidence at near the Brewster condition to said sample system alignment surface, interact with said sample system and enter said reflection and/or transmission detector to the end that data as a function of angle-of-incidence is acquired; and applying said computational means which is programmed with a mathematical model for said sample system to the end that an absolute value for at least one index of refraction selected from the group consisting of $(n_x)$, $(n_y)$ and $(n_z)$ is/are directly determined, and, if desired or required, from previously determined values for $(\Delta n_{xy})$, $(\Delta n_{xz})$ and $(\Delta n_{yz})$, determining absolute values for $(n_x)$, $(n_y)$ or $(n_z)$ not directly evaluated.

5.
Optionally causing a spectroscopic beam of electromagnetic radiation originating from said source of a beam of electromagnetic, (which beam of electromagnetic radiation is preferably essentially linearly polarized), to approach said alignment surface of said sample system along a plurality of angles-of-incidence to said sample system alignment surface, interact with said sample system and enter said transmission and/or reflection detector, to the end that data as a function of wavelength and angle-of-incidence is acquired; and applying said computational means which is programmed with a mathematical model for said sample system to the end that dispersion data for at least one index of refraction selected from the group consisting of $(n_x)$, $(n_y)$ and $(n_z)$ is determined.

FIG. 3 CONT.

METHOD FOR EVALUATING SAMPLE SYSTEM ANISOTROPIC REFRACTIVE INDICES AND ORIENTATIONS THEREOF IN MULTIPLE DIMENSIONS

This Application is a CIP of Provisional Application Serial No. 60/126,552 filed Mar. 26, 1999.

TECHNICAL FIELD

The present invention relates to characterization of sample systems, and more particularly is a method of evaluating anisotropic sample system refractive indices, and orientations thereof, with respect to an alignment surface of said sample system, in multiple dimensions. The preferred method involves a sequence of steps which allows overcoming mathematical model parameter correlation during mathematical regression parameter evaluation, even though individually, steps of the present invention method wherein anisotropic refractive indices, or differences therebetween are evaluated, require that only a relatively simple one dimensional data set be acquired.

BACKGROUND

While many of the steps of the present invention can be practiced utilizing spectrophotometer systems, said present invention methodology is preferably practiced utilizing an ellipsometer/polarimeter system. The primary difference between ellipsometry/polarimetry and spectrophotometry is that the former evaluates changes in angle between orthogonal components of a polarized electromagnetic beam of radiation in addition to magnitudes, or more precisely a ratio of magnitudes thereof, as a result of interaction with a sample system. In that light it is further noted that ellipsometry is a well known means by which to monitor optical and physical properties of sample systems, (eg. an anisotropic substrate which possibly comprises thin films on a surface thereof). In brief, ellipsometry provides that a polarized beam of electromagnetic radiation of one or more wavelengths is caused to impinge upon a sample system along one or more angles of incidence and interact, (eg. reflect from or transmit through), therewith. Beams of electromagnetic radiation can be considered as comprised of two orthogonal components, (ie. "P" and "S"), where "P" identifies a plane which contains both an incident beam of electromagnetic radiation, and a normal to an investigated alignment surface of a sample system being investigated, and where "S" identifies a plane perpendicular to the "P" plane and parallel to said alignment surface of said sample system. A change in polarization state in a polarized beam of electromagnetic radiation caused by said interaction with a sample system, is representative of properties of said sample system. (Note that Polarization State basically refers to a magnitude of a ratio of orthogonal component magnitudes in a polarized beam of electromagnetic radiation, and a phase angle therebetween, although absolute values for orthogonal components and "handedness", and even percent of polarization are further full polarization state determining factors). Generally two well known angles, (PSI and DELTA), which characterize a sample system at a given Wavelength and Angle-of-Incidence, are determined by analysis of data which represents change in polarization state. PSI is a ratio of the "P" and "S" component magnitudes, and DELTA is the phase angle therebetween. Again, spectrophotometer systems do not provide data regarding DELTA related phase angle, and often provide absolute rather than PSI ($\psi$) type ratio intensity values. For instance, utilizing a transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

to represent mathematically how a sample system affects a polarized electromagnetic beam, with Epi and Esi orthogonal components, and which is caused to interact therewith, it is to be appreciated that an ellipsometer/polarimeter system might return an on-diagonal ratio:

$$(Tpp/Tss) = \operatorname{Tan}\left(\psi_{\frac{pp}{ss}}\right)\left(e^{i\Delta\frac{pp}{ss}}\right);$$

and off-diagonal ratios:

$$(Tsp/Tss) = \operatorname{Tan}\left(\psi_{\frac{sp}{ss}}\right)\left(e^{i\Delta\frac{sp}{ss}}\right);$$

$$(Tps/Tss) = \operatorname{Tan}\left(\psi_{\frac{ps}{ss}}\right)\left(e^{i\Delta\frac{ps}{ss}}\right);$$

$$(Tsp/Tpp) = \operatorname{Tan}\left(\psi_{\frac{sp}{pp}}\right)\left(e^{i\Delta\frac{sp}{pp}}\right);$$

$$(Tps/Tpp) = \operatorname{Tan}\left(\psi_{\frac{ps}{pp}}\right)\left(e^{i\Delta\frac{ps}{pp}}\right);$$

as a function of a selection from the group consisting of:
- angle-of-incidence;
- wavelength; and
- sample system rotation about a normal to said alignment surface.

A spectrophotometer system, however, might return Tpp, Tss, Tsp and/or Tps as a function of angle-of-incidence; wavelength; and/or sample system rotation about a normal to said alignment surface. It is to be understood that a reflection Jones Matrix $$\begin{bmatrix} Epo \\ Eso \end{bmatrix} = \begin{bmatrix} Rpp & Rsp \\ Rps & Rss \end{bmatrix} \begin{bmatrix} Epi \\ Esi \end{bmatrix}$$

could have also been utilized for said demonstration, and that generally the present invention method can be practiced utilizing data obtained with ellipsometer, polarimeter or spectrophotometer systems configured in transmission or reflection modes, and/or combinations thereof in any steps thereof, wherein functionality is preserved.

Continuing, Ellipsometer Systems generally include a source of a beam of electromagnetic radiation, a Polarizer, which serves to impose a linear state of polarization on a beam of electromagnetic radiation, a Stage for supporting a sample system, and an Analyzer which serves to select a polarization state in a beam of electromagnetic radiation after it has interacted with a sample system, and passed to a Detector System for analysis therein. As well, one or more Compensator(s) can be present and serve to affect a phase angle between orthogonal components of a polarized beam of electromagnetic radiation. This is especially important where it is necessary to determine the "Handedness" of a polarized beam of electromagnetic radiation.

A number of types of ellipsometer systems exist, such as those which include rotating elements and those which include modulation elements. Those including rotating elements include Rotating Polarizer (RP), Rotating Analyzer (RA), Rotating Compensator (RC) and Modulation element (ME). It is noted that Rotating Compensator Ellipsometer Systems do not demonstrate "Dead-Spots" where obtaining data is difficult. They can read PSI ($\psi$) and DELTA ($\Delta$) of a sample system over a full Range of Degrees with the only limitation being that if PSI becomes essentially zero (0.0), one can not then determine DELTA as there is not a sufficient PSI ($\psi$) Polar Vector Length to form the angle between the PSI ($\psi$) Vector and an "X" axis. In comparison, Rotating Analyzer and Rotating Polarizer Ellipsometers have "Dead Spots" at DELTA's ($\Delta$'s) near 0.0 or 180 Degrees and Modulation Element Ellipsometers also have "Dead Spots" at PSI ($\psi$) near 45 Degrees. The present invention method can be practiced with essentially any ellipsometer system.

A Search of Patents relevant to the present invention has identified very little of specific relevance. One Patent, to Dill, U.S. Pat. No. 4,053,232 describes a Rotating-Compensator Ellipsometer System, which operates utilizes monochromatic light. Two Patents which identify systems which utilize Polychromatic light in investigation of sample systems are described in U.S. Pat. Nos. 5,596,406 and 4,668,086, to Rosencwaig et al. and Redner, respectively, were also identified. Also identified is a Patent to Woollam et al, U.S. Pat. No. 5,373,359 as it describes a Rotating Analyzer Ellipsometer System which utilizes white light. Patents continued from the 359 Woollam et al. Patent are, U.S. Pat. No. 5,504,582 to Johs et al. and U.S. Pat. No. 5,521,706 to Green et al. Said 582 Johs et al. and 706 Green et al. Patents describe use of polychromatic light in a Rotating Analyzer Ellipsometer System. A Patent to Bernoux et al., U.S. Pat. No. 5,329,357 is identified as it describes the use of optical fibers as input and output means in an ellipsometer system. A Patent to Chen et al., U.S. Pat. No. 5,581,350 is identified as it describes the application of regression in calibration of ellipsometer systems.

A particularly interesting Patent to Herzinger, U.S. Pat. No. 5,835,222, is identified, and incorporated hereinto by reference, as it describes an ellipsometric based method for identifying the orientation of an optical axis in a material system with respect to an alignment surface thereof. One recitation of the method of the 222 Patent method of qualifying a material system as having an optical axis oriented in a desired locus with respect to an alignment surface thereof, comprises, in a functional order, the steps of:

a. by ellipsometric techniques determining the magnitudes of at least one member of the group consisting of:
real; imaginary; and a combination of real and imaginary components;

for at least one ratio of components of a material system representing transmission Jones matrix as a function of at least one member of the group consisting of:
wavelength; and
"P" plane angle-of-incidence of an investigating polarized beam of electromagnetic radiation to an alignment surface of said material system; and
optical axis radial direction rotation angle;

said at least one ratio of material system representing transmission Jones matrix components being selected from the group consisting of:
on-diagonal ratio:

(Tpp/Tss);

and off-diagonal ratios:

(Tsp/Tss);

(Tps/Tss);

(Tsp/Tpp);

(Tps/Tpp);

where Tpp, Tss, Tps and Tsp are the components of a two dimensional material system representing transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

which material system representing transmission Jones matrix describes the change in polarization state between said incident and transmitted portions of said beam of electromagnetic radiation;

b. providing a mathematical model of said material system comprising at least one deviation angle calibration parameter which represents a non-coincidence of said optical axis with a desired locus with respect to said alignment surface, said mathematical model serving to relate indices of refraction, thickness and optical axis direction over a range of at least one member of the group consisting of:
wavelength; and
"P" plane angle-of-incidence of an investigating polarized beam of electromagnetic radiation to an alignment surface of said material system; and
optical axis radial direction rotation angle;

c. performing a regression procedure of said mathematical model onto said magnitude of at least one member of the group consisting of:
real;
imaginary; and
a combination of real and imaginary components;

of at least one step a. selected ratio of material system representing transmission Jones matrix components as a function of at least one member of the group consisting of:
wavelength;
"P" plane angle-of-incidence of an investigating polarized beam of electromagnetic radiation to an alignment surface of said material system; and
optical axis radial direction rotation angle;

such that said at least one deviation angle calibration parameter is evaluated.

Material systems are accepted if the deviation angle is small enough to fall within selected guidelines.

Said method of qualifying a material system as having an optical axis oriented in a desired locus with respect to an alignment surface thereof can further comprising the step of;

e. plotting magnitude(s) of at least one determined on-diagonal (Tpp/Tss) and/or off-diagonal ratio(s) selected from the group consisting of:

(Tps/Tpp) and (Tsp/Tss) and (Tps/Tss) and (Tsp/Tpp);

with respect to at least one parameter selected from the group consisting of:
wavelength;
"P" plane angle-of-incidence of an investigating polarized beam of electromagnetic radiation to an alignment surface of said material system; and
optical axis radial direction rotation angle;

and accepting said material system based upon observing said plot(s) only if said plot(s) essentially match known "template" plots.

Another Patent, U.S. Pat. No. 5,757,494 to Green et al., is identified as it describes a method for enabling investigation of a sample system with ellipsometer systems, even in ellipsometric PSI and/or DELTA regions wherein said ellipsometer system is, without the invention, "blind", (eg. DELTA of (0.0) or (180) degrees) in Rotating Polarizer and Rotating Analyzer Ellipsometer Systems, and/or (PSI or (45) degrees in Modulation Element Ellipsometer Systems). Said 494 Patent describes a method of determination of sample system PSI and DELTA values with improved accuracy and precision comprising utilizing a variable compensator, said method comprising in a functional order, the steps of:

a. providing an ellipsometer system selected from the group consisting of:
   modulation element, rotatable element and rotating element;
   which ellipsometer system enables accurate and precise determination of PSI and DELTA values of essentially any investigatable sample system; said ellipsometer system comprising means for setting at least one polarization state in a beam of polarized light and means for identifying, and means for monitoring a polarization state in said polarized beam of light, after an interaction thereof with a sample system;
   between said means for setting at least one polarization state in a beam of polarized light and said means for monitoring a polarization state in said polarized beam of light, there being present at least one adjustable means for controlling an ellipsometric phase angle between orthogonal components in a polarized beam of light, which adjustable means for controlling an ellipsometric phase angle, in use, allows sequentially setting a plurality of ellipsometric phase angles between orthogonal components in a polarized beam of light which is caused by said ellipsometer system to interact with a sample system, such that in use said ellipsometric phase angle can be set sequentially through a plurality of settings while ellipsometric data is obtained by said means for monitoring a polarization state in said polarized beam of light at at least two selected settings of said at least one adjustable means for controlling an ellipsometric phase angle; which obtained ellipsometric data can be utilized in determination of PSI and DELTA values of an investigated sample system, where said determination of said PSI and DELTA values includes compensating for the effects on said obtained ellipsometric data of said at least two selected setting of said at least one adjustable means for controlling an ellipsometric phase angle, on said obtained ellipsometric data;
   said ellipsometer system being further comprised of computational means which performs determination of investigated sample system PSI and DELTA values, which computational means utilizes data obtained with said at least one adjustable means for controlling ellipsometric phase angle between orthogonal components in a polarized beam of light, being set to at least two selected settings, and which computational means performs compensation of the effects of said at least one adjustable means for controlling ellipsometric phase angle between orthogonal components, on said utilized ellipsometric data obtained at said at least two selected settings of said at least one adjustable means for controlling ellipsometric phase angle between orthogonal components in determining sample system PSI and DELTA values;

b. placing a sample system to be investigated into said ellipsometer system and causing a beam of polarized light from said means for setting at least one polarization state in a beam of polarized light to interact therewith and enter said means for monitoring a polarization state;

c. adjusting said at least one adjustable means for controlling ellipsometric phase angle between said orthogonal components to be sequentially set to a plurality of settings while ellipsometric data is obtained by said means for monitoring a polarization state in said polarized beam of light at at least two selected settings from said plurality settings of said at least one adjustable means for controlling a value of ellipsometric phase angle between said orthogonal components;

d. causing said computational means to determine investigated sample system PSI and DELTA values by a method which performs compensation of the effects of said at least one adjustable means for controlling ellipsometric phase angle between orthogonal components in a polarized beam of light on said ellipsometric data obtained at said at least two selected settings of said at least one adjustable means for controlling ellipsometric phase angle between orthogonal components in a polarized beam of light which is caused to interact with a sample system, in determining sample system PSI and DELTA values; and e. optionally determining at least some of members of the group consisting of:
   the "Handedness";
   Stokes Vector; and
   Jones and Mueller Matrix components;

of said polarized beam of light and investigated sample system.

(It is noted that the computational means can be any computer system with sufficient memory and processing capability).

Said method can include obtaining data comprising a plurality of relative magnitude ratios of orthogonal components and phase angles between orthogonal components are obtained, at least some of which plurality of ellipsometric relative magnitude ratios of orthogonal components and measured ellipsometric phase angles between orthogonal components correspond to sequential adjusted settings of ellipsometric relative magnitude ratios of orthogonal components present in said beam of polarized light, said sequential adjusted settings being effected by adjustment of at least one member of the group consisting of:

said means for setting at least one polarization state in a beam of polarized light; and
said means for identifying a polarization state in said polarized beam of light;

and in which said computational means is also caused to perform compensation of the effects of said sequential adjusted settings of ellipsometric relative magnitude ratios of orthogonal components present in said beam of polarized light which is caused by said ellipsometer system to interact with a sample system, in determining investigated sample system PSI and DELTA values. Said method can also involve obtaining a plurality of ellipsometric phase angles between orthogonal components which are effected at each sequential adjusted setting of ellipsometric relative magnitude ratio of orthogonal components present in said beam of polarized light which is caused by said ellipsometer system to interact with a sample system. Said 494 is disclosed as the at least one adjustable means for controlling ellipsometric phase angle between said orthogonal components to be sequentially set to a plurality of settings while ellipsometric data is obtained is a compensator which is typically utilized in practice of the present invention to determine "Handedness", that is, if a value for ($\Delta n_{xy}$) which is determined by present invention methodology is positive or negative.

A recent Patent to Johs et al., U.S. Pat. No. 5,872,630, is also disclosed as it describes rotating compensator ellipsometer system and a method of evaluating sample system characteristics, involving application of mathematical regression onto data acquired by application of electromagnetic beams thereto. Said 630 Patent Claims a spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:

before said stage for supporting a material system; and after said stage for supporting a material system; and both before and after said stage for supporting a material system;

such that when said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system. Also Claimed is a regression based method of calibrating a spectroscopic rotating compensator material system investigation system comprising the steps of:

a. providing a spectroscopic rotating compensator material system investigation system as described;

b. developing a mathematical model of said spectroscopic rotating compensator material system investigation system which comprises as calibration parameter variables polarizer azimuthal angle orientation, present material system PSI, present material system DELTA, compensator azimuthal angle orientation(s), matrix components of said compensator(s), and analyzer azimuthal angle orientation, which mathematical model is effectively a transfer function which enables calculation of electromagnetic beam intensity as a function of wavelength detected by a detector element, given intensity as a function of wavelength provided by said source of a polychromatic beam of electromagnetic radiation;

c. causing a polychromatic beam of electromagnetic radiation produced by said source of a polychromatic beam of electromagnetic radiation, to pass through said polarizer, interact with a material system caused to be in the path thereof, pass through said analyzer, and interact with said dispersive optics such that a multiplicity of essentially single wavelengths are caused to simultaneously enter a corresponding multiplicity of detector elements in said at least one detector system, with said polychromatic beam of electromagnetic radiation also being caused to pass through said compensator(s) positioned at a location selected from the group consisting of:

before said stage for supporting a material system;

after said stage for supporting a material system; and both before and after said stage for supporting a material system;

d. obtaining an at least two dimensional data set of intensity values vs. wavelength and a parameter selected from the group consisting of:

angle-of-incidence of said polychromatic beam of electromagnetic radiation with respect to a present material system; and azimuthal angle rotation of one element selected from the group consisting of:

said polarizer; and said analyzer;

over time, while at least one of said at least one compensator(s) is caused to continuously rotate;

e. performing a mathematical regression of said mathematical model onto said at least two dimensional data set, thereby evaluating calibration parameters in said mathematical model;

said regression based calibration procedure evaluated calibration parameters serving to compensate said mathematical model for non-achromatic characteristics and non-idealities of said compensator(s), and for azimuthal angles of said polarizer. Said 630 Patent is disclosed for general insight to ellipsometric procedure.

Other Patents to Johs et al. are U.S. Pat. Nos. 5,666,201 and 5,805,285. Said Patents, it is noted, describe, respectively, a spectroscopic ellipsometer and a spectroscopic spectrophotometer system, wherein a spectroscopic beam of electromagnetic radiation is caused to interact with a dispersive optics to the end that multiple orders of wavelengths are produced and detected.

Scientific articles which are of direct interest, and which are included herewithin by reference are:

"Optical Characterization Of Anisotropic Plastics", Hilfiker, Herzinger, Bungay, Woollam & Elman, Optical Interference Coatings, Op. Soc. Am, Tech. Dig. Series, Vol. 9, ((1998).

"Characterization of Bi-Axially-Stretched Plastic Films By Generalized Ellipsometry", Elman, Greener, Herzinger & Johs, Thin Solid Films, 313–314 (1998).

"Phase And Microstructure Investigations Of Boron Nitride Thin Films By Spectroscopic Ellipsometry In The Visible And Infrared Spectral Range", Franke, Schubert, Neumann, Tiwald, Thompson, Woollam, Hahn & Richter, J. Appl. Phys. 82(6), (September 1997).

"Determination Of Optical Anisotropy In Calcite From Ultraviolet To Mid-Infrared By Generalized Ellipsometry", Thompson, DeVries, Tiwald, & Woollam, Thin Solid Films, 313–314 (1998).

Additionally, an article by Johs, titled "Regression Calibration Method For Rotating Element Ellipsometers", which appeared in Thin Film Solids, Vol. 234 in 1993 is also identified as it predates the Chen et al. 350 Patent and describes an essentially similar approach to ellipsometer calibration. An article by Jellison Jr. titled "Data Analysis for Spectroscopic Ellipsometry", Thin Film Solids, 234, (1993) is identified as it describes a method for determining the accuracy with which certain data points can be measured, which information allows adding a weighting factor to a curve fitting regression procedure as applied to a multiplicity of data points, said weighting factor serving to emphasize the effect of more accurate and precise data. A book by Azzam and Bashara titled "Ellipsometry and Polarized light" North-Holland, 1977 is disclosed and incorporated herein by reference for general theory. An article by Collins titled "Automated Rotating Element Ellipsometers: Calibration, Operation, and Real-Time Applications", Rev. Sci. Instrum. 61(8), August 1990 is identified as it provides insight into rotating element ellipsometers. An article by Kleim et al. titled "Systematic Errors in Rotating-Compensator Ellipsometry" published in J. Opt. Soc. Am./Vol. 11, No. 9, September 1994 is identified as it describes calibration of rotating compensator ellipsometers. An Article by An and Collins titled "Waveform Analysis With Optical Multichannel Detectors: Applications for Rapid-Scan Spectroscopic Ellipsometer", Rev. Sci. Instrum., 62 (8), August 1991 is also identified as it discusses effects such as Detection System Error Characterization, Stray Light, Image Persistence etc., and calibration thereof. Also disclosed are articles by Schubert et al. which describe "Generalized Ellipsometry". The first thereof is titled "Extension Of Rotating-Analyzer Ellipsometry To Generalized Ellipsometry: Determination Of The Dielectric Function Tensor From Uniaxial TiO2", J. Opt. Soc. Am. A. 13, (1996). The second such article is authored by M. Schubert alone and is titled "Polarization Dependent Parameters Of Arbitrary Anisotropic Homogeneous Epitaxial Systems", Phys. Rev. B 53, (1996). The third such article is titled "Generalized Transmission Ellipsometry For Twisted Biaxial Dielectric Media: Application To Chiral Liquid Crystals", J. Opt. Soc. Am. A/Vol. 13, No. 9 (1996). The Schubert et al. articles, it is noted, describe ellipsometer systems which have rotatable sample system supporting stages, and primarily focus on investigation of sample systems, utilizing said ellipsometer systems, which sample systems have isotropic "in-plane" refractive indices, (ie. where $n_x = n_y$). Further identified for authority regarding mathematical regression is a book titled Numerical Recipes in "C", 1988, Cambridge University Press.

In view of the foregoing, a need remains for methodology for evaluating anisotropic refractive indices, and orientations thereof, in three dimensions.

DISCLOSURE OF THE INVENTION

The present invention is an ellipsometer/polarimeter, and/or spectrophotometer based method of determining values for anisotropic refractive indices $(n_x)$, $(n_y)$ and $(n_z)$ in, respectively, "x", "y" and "z" directions in a sample system, which "x", "y" and "z" directions have a determinable relationship to the orientation of an alignment surface of said sample system. The present invention method, in its preferred embodiment, because of its sequence of steps and utilization of parameter values and/or data acquired in earlier steps in later steps, requires acquisition of relatively simple and easy to acquire data sets of only one (1) dimension where refractive indices $(n_x)$, $(n_y)$ and $(n_z)$ or differences therebetween $(\Delta n_{xy})$; and $(\Delta n_{xz}$ or $\Delta n_{yz})$ are evaluated. However, variations of said preferred method allow for use of multiple dimension data sets in mathematical regression based determination of deviation from perpendicular to a sample system alignment surface regarding the direction of an out-of-plane $(n_z)$ refractive index, or where, for instance, separately identifiable steps are combined, or where it is desired to determine dispersion characteristics of one or more refractive indices which have previously been evaluated at a single wavelength. The essence of the preferred present invention method can be recited as sequentially involving at least four basic steps, said four basic steps being:

1

Determining the precise orientation of a third orthogonal index $(n_z)$ of refraction which projects essentially perpendicular to an alignment surface of a sample system, said alignment surface being characterized by two essentially in-plane orthogonal, (ie. $(n_x)$ and $(n_y)$), indices of refraction;

2

Causing a spectroscopic beam of electromagnetic radiation originating from a source of a beam of electromagnetic radiation, (which spectroscopic beam of electromagnetic radiation is preferably essentially linearly polarized and is comprised of a plurality of wavelengths for which said sample system is essentially transparent), to approach said alignment surface of said sample system along a locus which is essentially co-incident with the orientation of the third orthogonal index $(n_z)$ of refraction, at least partially transmit through said sample system and enter a transmission detector to the end that a one-dimensional data set as a function of wavelength is acquired; and applying a computational means which is programmed with a mathematical model for said sample system to the end that a value for the difference between the in-plane $(\Delta_{xy})$ indices of refraction and the Euler angle orientations of said essentially in-plane orthogonal $(n_x)$ $(n_y)$ indices of refraction are determined;

3

Causing a beam of electromagnetic radiation originating from said source of a beam of electromagnetic radiation, (which beam of electromagnetic radiation is preferably essentially linearly polarized and is comprised of at least one wavelength), to approach said alignment surface of said sample system along a plurality of near normal angles-of-incidence to said sample system alignment surface, interact with said sample system and enter said transmission and/or reflection detector to the end that a one dimensional data set as a function of angle-of-incidence is acquired; and applying said computational means which is programmed with a mathematical model for said sample system to the end that a value for the difference between at least one out-of-plane combination of indices of refraction selected from the group consisting of $(\Delta_{xz})$, and $(\Delta n_{yz})$ is determined; and

4

Causing a beam of electromagnetic radiation originating from said source of a beam of electromagnetic radiation, (which beam of electromagnetic radiation is preferably essentially linearly polarized and is comprised of at least one wavelength), to approach said alignment surface of said sample system along a plurality of angles-of-incidence at near the Brewster condition to said sample system alignment surface, interact with said sample system and enter said reflection and/or transmission detector to the end that data as a function of angle-of-incidence is acquired; and applying said computational means which is programmed with a mathematical model for said sample system to the end that an absolute value for at least one index of refraction selected from the group consisting of $(n_x)$, $(n_y)$ and $(n_z)$ is/are directly determined, and, if desired or required, from previously determined values for $(\Delta n_{xy})$, $(\Delta n_{xz})$ and $(\Delta n_{yz})$, determining absolute values for $(n_x)$, $(n_y)$ or $(n_z)$ not directly evaluated.

It is believed that the present invention Patentability is found in two areas:

1. specific method step sequences, which sequences, in later steps thereof, utilize results secured in earlier steps thereof, in mathematical, (eg. square error reducing regression), procedures which operate on said data acquired in said later steps; and 2. only one dimensional data sets need be generated in steps of the preferred embodiment, where values for refractive indices ($n_x$), ($n_y$) and ($n_z$) or differences therebetween ($\Delta n_{xy}$); and ($\Delta n_{xz}$) or ($\Delta n_{yz}$) are evaluated.

Continuing, while the present invention can be practiced utilizing various optical systems, including polarimeters or spectrophotometers, ellipsometers are disclosed as the preferred systems. In that light, for demonstrative insight, the following brief description of ellipsometric procedure is presented. The practice of ellipsometry requires providing an ellipsometer system, (see FIG. 1), comprised elements selected from a group including:

1. a source of a beam of electromagnetic radiation (LS);
2. a polarizer (P);
3. a stage for supporting a sample system (STG);
4. an analyzer (A);
5. a reflection detector (DET-REFLECTION);
6. a transmission detector (DET-TRANSMISSION);
7. a compensator ((C), (C') (C")) at some point between said polarizer (P) and analyzer (A); and
8. a modulation element at some point between said polarizer (P) and analyzer (A);

and it is to be understood that typically associated with an ellipsometer system is a computational means which is programmed with a mathematical model of the ellipsometer system and of a sample system being investigated. The mathematical model of the ellipsometer system typically comprises matrices, or mathematical equivalents, for the source of the beam of electromagnetic radiation, for the polarizer and for the analyzer and detector, and comprises a mathematical model for the sample system, including thicknesses and refractive indices of various surface layers, and parameters which identify anisotropic refractive indices ($n_x$), ($n_y$), ($n_z$), and directions "x", "y" and "z" thereof, and differences between ($n_x$) and ($n_y$), ($\Delta n_{xy}$) and differences between ($n_x$) and ($n_z$), ($\Delta n_{xz}$) and differences between ($n_y$) and ($n_z$), ($\Delta n_{yz}$). Said mathematical model can also include Jones Matrix elements. Said computational means also includes a square error reducing routine for fitting numbers to said mathematical model parameters in view of experimental data obtained when a beam of single wavelength, or polychromatic, electromagnetic radiation is caused to interact with a sample system, (which is oriented in some desired state of rotation about an axis perpendicular to the alignment surface thereof), at one or various angles of incidence. Also, while it is typical that a beam of electromagnetic radiation which is caused to transmit through or reflect from a sample system surface will have orthogonal components therein retarded by differing amounts, it is further typical that said retardation difference is usually not so large that the intensity of the emerging transmitted or reflected electromagnetic beam can not be found by assuming mathematical coherent addition of said orthogonal components. However, particularly where a sample system demonstrates a large degree of anisotropy, it can occur that orthogonal components of an electromagnetic beam caused to interact therewith will be subjected to greatly differing amounts of retardation by interaction therewith. Where this occurs, it is necessary to assume orthogonal beam electric field components add incoherently to arrive at a valid intensity. In some cases assuming partial coherent:

$$I=(E_1+E_2+\ldots E_N)^*(E_1+E_2+\ldots E_N)^*$$

and partial incoherent:

$$I=(E_1^*E_1^*)+(E_2^*E_2)+\ldots (E_N^*E_N^*)$$

addition of orthogonal electric field components can be appropriate, (eg. where pertinent data is obtained with the ellipsometer system set in a reflection mode configuration, and where a reflection detector is utilized and a transparent sample system does not have a backside thereof roughened). It is noted that the J. A. Woollam Co. Inc. W-VASE (Registered Trademark), program includes Backside Reflection Compensation capability. Note, the partitioning of a beam of electromagnetic radiation into portions which present separately with electric field components which add coherently, and incoherently, as a result of interaction with a patterned substrate, is described in a recently Allowed U.S. Pat. No. 5,936,734 to Johs and Herzinger.

It is further beneficial to emphasize that data sets can be produced by ellipsometer, polarimeter and spectrophotometer systems, which are single or multiple dimensional. That is, for instance, data as a function of:

a. wavelength; and/or
b. angle-of-incidence of a beam of electromagnetic radiation with respect to a normal to a sample system alignment surface; and/or
c. rotation of said sample system about said normal to a sample system alignment surface;

can be obtained. Further, most prior art methodology identifies the number of parameters in a mathematical model of a sample system which require evaluation, and based thereupon determine the dimensionality of data set which is required. Simultaneous mathematical regression of the mathematical model onto the sufficient data set is typically utilized to arrive at values, and confidence intervals thereof, for all mathematical model parameters. It is also noted that the reason a data set must be of "sufficient" dimensionality, is that the procedure of mathematical regression evaluation of values for parameters in a mathematical model can fail because of "correlation" between parameters, and only a sufficiently "strong" data set can avoid this pit-fall. Correlation, it is noted, refers to the situation wherein, for instance, two parameters are interrelated, such as components of a product term, which product term is directly evaluated by a mathematical regression onto a data set, (eg. refractive index (n) multiplied by a sample system thickness (t)), which product term can be arrived at by many combinations of the (n) and (t) components thereof. Use of a sufficiently strong data set, (eg. data sets obtained from two sample systems of similar refractive index (n) but different thicknesses (t1) and (t2)), in a mathematical regression procedure, can however, allow independent evaluation of the components, (ie. (n) and (t1) and (t2), of the product. In that light, it is again pointed out that the preferred embodiment of the present invention methodology provides a sequence of steps which enables use of a single dimensioned data set at each step where anisotropic refractive indices or differences therebetween are evaluated, while avoiding correlation of evaluated mathematical model parameters. This is achieved by limiting the number of parameters to be evaluated at each step where mathematical regression is applied.

Continuing, a present invention method of determining values for anisotropic refractive indices ($n_x$), ($n_y$) and ($n_z$) in, respectively, "x", "y" and "z" directions in a sample system begins with the providing of an ellipsometer or polarimeter or spectrophotometer system comprised of selections from the group consisting of:

1. a source of a beam of electromagnetic radiation;
2. a polarizer;
3. a stage for supporting a sample system;
4. an analyzer;
5. a reflection detector;
6. a transmission detector;
7. a compensator at some point between said polarizer and analyzer;
8. a modulation element at some point between said polarizer and analyzer; and
9. a computational means which is programmed with a mathematical model for said sample system, said mathematical model serving to relate indices of refraction, thickness and optical axis direction over a range of at least one member of the group consisting of:
   wavelength;
   "P" plane angles-of-incidence of an investigating polarized beam of electromagnetic radiation to an alignment surface of said material system; and
   optical axis radial direction rotation angle;
which computational means includes a mathematical, (eg. square error reducing), routine for fitting numbers to said mathematical model parameters in view of experimental data, and which can include analysis capabilities based upon accounting for coherent and incoherent addition of electromagnetic components in calculation of intensity, as occurs where backside reflections are present. (Note, the Patent to Johs, U.S. Pat. No. 5,872,630, discussed in the Background Section of this Disclosure describes use of such a computational means for use in mathematical modeling in the case of a Rotating Compensator Ellipsometer System, and wherein mathematical regression is performed onto a two-dimensional data set).

(It is noted that the terminology "computational means" includes any computer system with sufficient input, memory, processing capability and output means).

As alluded to above, said method further involves providing a sample system having two essentially in-plane ($n_x$) ($n_y$) orthogonal indices of refraction in an alignment surface thereof and a third ($n_z$) index of refraction which projects essentially perpendicular to said alignment surface of said sample system, then determining the thickness of said sample system as well as a range of wavelengths for which said sample system is essentially transparent. (It should be appreciated that the two in-plane ($n_x$) ($n_y$) orthogonal indices of refraction typically are of different values). Said thickness determination is often accomplished by non-ellipsometric techniques, (eg. by use of calipers), although it is again noted that if at least two sample systems which are similar in composition, but of different thickness dimensions are simultaneously investigated, the J. A. Woollam Co. W-VASE (Registered Trademark) program allows simultaneous regression onto data obtained from investigation of both said sample systems, and that generally allows breaking correlation between thickness and refractive indices with the result that a sample system thickness can be obtained by the ellipsometric techniques.

Continuing, said method further involves placing said sample system on the stage for supporting a sample system so that said alignment surface of said sample system is accessible by a beam of electromagnetic radiation originating from said source of a beam of electromagnetic radiation.

Said method also involves determining the precise orientation of the third ($n_z$) index of refraction which projects essentially perpendicular to said alignment surface thereof, by a technique such as described in U.S. Pat. No. 5,835,222 to Herzinger, and briefly disclosed in the Background Section of this Disclosure. This step, it is noted, can optionally involve the acquisition of a two dimensional data set, as deviation of an ($n_z$) direction from a precise normal to an alignment surface of a sample system, as well as the direction of a "P"-plane projection thereof in the alignment surface of the sample system can be unknown. However, qualitative observation of plotted one dimensional data sets prior to proceeding with any data set acquisition for use in quantitative regression procedures, can provide insight to good approximate starting values for the unknown related to the ($n_z$) direction deviation from a precise normal to an alignment surface of a sample system, as well as the direction of a "P"-plane projection thereof in the alignment surface of the sample system. For instance, obtaining data utilizing a beam of electromagnetic radiation directed normal to an alignment surface of a sample system as a function of sample system rotation about said normal to said alignment surface can, in some cases, provide a sufficient data set for use in a regression procedure that allows precise characterization of the direction of ($n_z$) direction deviation from a precise normal to an alignment surface of a sample system, as well as the direction of a "P"-plane projection thereof in the alignment surface of the sample system. Such a non-limiting procedure, which sequentially requires obtaining only one dimensional data sets, comprises:

a. by ellipsometric techniques effectively obtaining a plot of a sample system PSI ($\psi$) vs. sample system rotation angle about a perpendicular to a surface of said sample system, and therefrom determining the in-plane angle at which the plane of incidence of said ellipsometric beam of electromagnetic radiation includes the direction of ($n_x$) or ($n_y$), by noting where minima and/or maxima occur in said effective plot; and
   b. with the plane of incidence of said ellipsometric beam of electromagnetic radiation positioned as determined in step a., so as to include the direction of ($n_x$) or ($n_y$), effectively obtaining a plot of a DELTA ($\Delta$) vs. ellipsometric electromagnetic beam angle-of-incidence about a normal to the surface of said sample system, and therefrom determining a minima and/or maxima symetry point in said effective plot, said minima and/or maxima symetry point being identifying of the projected direction of ($n_z$) in said ellipsometric electromagnetic beam plane of incidence;

such that sample system rotation angle PHI ($\phi$), about a perpendicular to the surface of said sample system, at which the ellipsometric beam of radiation plane of incidence includes the direction of ($n_z$), and the angle of said projected direction of ($n_z$) with respect to the normal to the sample system surface, are determined.

It is again emphasized at this point that the preferred method of the present invention requires that only one (1) dimensional data sets need be obtained when practicing any of the steps of the present invention method, and it is the case that only one (1) dimensional data sets need be obtained in the steps which directly follow wherein anisotropic refractive indices or differences therebetween are evaluated.

In the following, it should be kept in mind that the present invention method steps which result in evaluating ($\Delta n_{xy}$); and ($\Delta n_{xz}$) or ($\Delta n_{yz}$), can be practiced in either order. That is, the steps leading to evaluation of ($\Delta n_{xy}$) can be determined first, or the steps leading to evaluation of ($\Delta n_{xz}$) or ($\Delta n_{yz}$) can be practiced first. However, practically, it is preferred to practice the steps which allow determining ($\Delta n_{xy}$) first as if the order of steps is reversed such that ($\Delta n_{xz}$) or ($\Delta n_{yz}$) is determined first, then it might be required to practice the steps which provide ($\Delta n_{xy}$) and those which provide ($\Delta n_{xz}$) or ($\Delta n_{yz}$) itteratively more than once.

The preferred present invention method further then involves causing a spectroscopic beam of electromagnetic radiation originating from said source of a beam of electromagnetic radiation, (which spectroscopic beam of electromagnetic radiation is comprised of a plurality of wavelengths for which said sample system is transparent), to preferably become essentially linearly polarized and approach the alignment surface of a sample system along a locus which is essentially co-incident with the previously determined precise orientation of the third index of refraction ($n_z$). (This eliminates the effect of said third index of refraction ($n_z$) on orthogonal components of the beam of electromagnetic radiation and decreases sensitivity to absolute values of ($n_x$) and ($n_y$). A transmitted portion of said beam of electromagnetic radiation is caused to exit said sample system enter said transmission detector which mediates the collection of data therefore. (Note that where physical limitations do not prevent placement of a reflection detector, reflection data can also, or instead of, transmission data, be acquired and utilized). Said collected spectroscopic data, along with known sample system thickness and the projection direction of ($n_z$), is then analyzed by applying said computational means which is programmed with a mathematical model for said sample system, to the end that a value for the difference between the in-plane ($\Delta n_{xy}$) indices of refraction and the Euler angle PHI ($\phi$) orientations (see FIG. 2), of said in-plane orthogonal ($n_x$) and ($n_y$) indices of refraction are determined. This is typically achieved via application of a mathematical regression. Again, it is to be understood that aligning the beam of electromagnetic radiation along the direction of the third index of refraction ($n_z$) focuses the procedure on determination of the difference between the in-plane ($\Delta n_{xy}$) indices of refraction, and prevents said ($n_z$), and absolute values of ($n_x$) and ($n_y$) indices of refraction, from having any effect in this step. It is also to be appreciated that there is always ninety (90) degrees between said in-plane orthogonal ($n_x$) and ($n_y$) indices of refraction, and that obtaining Jones Matrix Element Intensities:

$Tpp$, $Tss$, $Tsp$ and/or $Tps$ or Intensities of Ratios of Jones Matrix Elements:

($Tpp/Tss$);

($Tsp/Tss$);

($Tps/Tss$);

($Tsp/Tpp$);

and/or ($Tps/Tpp$);

as a function of a one dimensional data set, (ie. as a function of wavelength), provides sufficiently strong data to allow evaluation of the difference between the in-plane ($\Delta n_{xy}$) indices of refraction and the Euler angle PHI ($\phi$) orientations of said in-plane orthogonal ($n_x$) ($n_y$) indices of refraction, relative to the measurement geometry "P" and "S" planes. In fact, where good approximation values for the previously determined direction of the third index of refraction ($n_z$) are known, it is possible to let it "float" as well during a regression procedure onto said one dimensional data set as a function of wavelength, and arrive at somewhat improved values therefore, as well as for ($\Delta n_{xy}$) and Euler angle orientations, in this step.

Continuing, a beam of electromagnetic radiation originating from said source of a beam of electromagnetic radiation, (which beam of electromagnetic radiation is comprised of at least one wavelength for which said sample system is essentially transparent), is preferably caused to become essentially linearly polarized and approach said alignment surface of said sample system along a plurality of angles-of-incidence, (eg. in a range including perhaps at least about negative twenty (−20) to positive twenty (+20) degrees and typically over a range of negative forty-five (−45) to positive forty-five (+45) degrees with respect to the direction of the ($n_z$) index of refraction, which is essentially normal to the alignment surface of a sample system), to said sample system surface, partially transmit through said sample system and partially reflect therefrom and enter said transmission and/or reflection detector, which mediates the collection of data therefore, as a function of angle-of-incidence. Thereafter, said computational means which is programmed with a mathematical model for said sample system is applied to said just acquired data along with already known system thickness and the value for the difference between the in-plane ($\Delta n_{xy}$) indices of refraction and the Euler angle orientations of said in-plane orthogonal ($n_x$) ($n_y$) indices of refraction and the orientation of the out-of-plane ($n_z$) to the end that a value for the difference between at least one out-of-plane combination of indices of refraction selected from the group consisting of:

($\Delta n_{xz}$);

and ($\Delta n_{yz}$);

and is determined. It should now also be appreciated that if ($\Delta n_{xy}$), and one of ($\Delta n_{xz}$) and ($\Delta n_{yz}$) is determined, then the third thereof is indirectly determined as well.

It is generally noted that where an electromagnetic beam of radiation impinges upon a sample system surface at a near-to-normal angle-of-incidence and even at upwards of 25 degrees thereto, where transmission data is obtained, the effects of absolute refractive index, (ie. $n_x$, $n_y$ and $n_z$), values are negligible. For this, and other reasons, values of ($\Delta n_{xy}$), ($\Delta n_{xz}$) and ($\Delta n_{yz}$) can be determined as just described, whereas absolute refractive index difference values are typically completely obscured during said determination. It is noted that, for instance, reflection ellipsometry practiced with an electromagnetic beam directed at a sample system surface at a near Brewster Angle angle-of-incidence, (which for semiconductors is approximately seventy-five (75) degrees), allows determination of absolute refractive index values, where sample system backside reflections are accounted for. (Backside reflections can be prevented by, for instance, "roughening-up" the backside of the investigated sample substrate). Generally then, near normal angles-of-incidence maximize sensitivity to differences in refractive indices, and oblique, near Brewster angle angles-of-incidence maximize sensitivity to absolute refractive indices effects. The present invention methodology advantageously utilizes this "separated-out" determination of ($\Delta_{xy}$), ($\Delta n_{xz}$) and/or ($\Delta n_{yz}$) by use of "near normal" angles of incidence during data acquisition utilizing transmission mode ellipsometry.

Continuing, the present invention method next involves causing a beam of electromagnetic radiation which originates from said source of a beam of electromagnetic radiation, which beam of electromagnetic radiation is comprised of at least one wavelength, to preferably become essentially linearly polarized and approach said surface of said sample system along a plurality of angles-of-incidence at near the Brewster condition to said sample system surface, partially reflect from said alignment surface of said sample system and enter said reflection detector which mediates the collection of data therefore as a function of angle-of-incidence. Thereafter, said computational means which is programmed with a mathematical model for said sample system, is applied to said acquired data along with already known system thickness and the value for the difference between the in-plane ($\Delta n_{xy}$) indices of refraction and the Euler angle orientations of said in-plane orthogonal ($n_x$) ($n_y$) indices of refraction are determined, and the known difference between at least one out-of-plane combination of indices of refraction selected from the group consisting of:

$(\Delta n_{xz})$;

and $(\Delta n_{yz})$;

to the end that an absolute value for at least one index of refraction selected from the group consisting of:

$(n_x)$;

$(n_y)$;

$(n_z)$;

is/are determined. Then, as required, utilizing previously determined values for ($\Delta n_{xy}$), ($\Delta n_{xz}$) and ($\Delta n_{yz}$), absolute values for all ($n_x$), ($n_y$) and ($n_z$) are determined.

It is noted that determination of at least one index of refraction selected from the group consisting of:

$(n_x)$;

$(n_y)$;

$(n_z)$;

can include accounting for sample system back-side reflections by, for instance, application of incoherent electric field component addition. The J. A. Woollam CO. W-VASE (Registered Trademark) software provides this capability.

It is further noted that determination of a value for the difference between the in-plane ($\Delta n_{xy}$) indices of refraction and the Euler angle orientations of said in-plane orthogonal ($n_x$) ($n_y$) indices of refraction typically involves obtaining and utilizing data acquired with said compensator in two positions, (eg. present and not-present), in order to specifically identify a non-ambiguous, "handedness" determined value for ($\Delta n_{xy}$).

It is emphasized that the foregoing specifies definite acquisition of transmission, or of reflection, data in the various steps. However, after the determination of the direction of the deviation of an ($n_z$) direction from a precise normal to an alignment surface of a sample system, as well as the direction of any in-plane projection thereof in the alignment surface of the sample system, it is generally the case that either transmission or reflection data can be utilized, where physical space limitations regarding placement of detectors etc. allow. This is because an electromagnetic beam, (of a wavelength at which a sample system is substantially transparent), which is caused to interact with a sample system by impinging on its alignment surface, partially transmits and partially reflects from said alignment surface of said sample system, with the portions of the beam which transmit and reflect being largely dependent on the angle of incidence of said electromagnetic beam to the alignment surface. As both the transmitted and reflected beams contain similar information, either transmission or reflection beams can then, where physically possible, be detected and utilized in essentially all steps and be within the scope of the present invention. Also, it must be appreciated that data acquired can be anisotropic intensity data or anisotropic ellipsometric data. However, in a practical sense, as the identification of the orientation of the ($n_z$) index of refraction can require evaluation of very small deviation angles from a perpendicular to an alignment surface of a sample system, it is usually necessary to utilize ellipsometric data obtained from a transmission detector to allow determination of said deviation angles, as transmission through a large thickness of an anisotropic sample substrate provides measurable data which typically does not appear in reflection data, especially when reflection data is complicated by back-side reflections and physical restraints of detector location placement.

It is again noted that qualitative steps can provide insight to the approximate orientation of ($n_z$) and further augment the recited present invention quantitative method. For instance, prior to any quantitative data acquisition, data obtained by use of electromagnetic beam investigation of the sample system can be plotted and subjected to visual evaluation to determine relative anisotropy effects of "in-plane" indices of refraction ($n_x$) and ($n_y$) on said beam of electromagnetic radiation which is caused to pass through a thickness (t) of a sample system. Said data can be ellipsometric or intensity, as a function of wavelength or angle-of-incidence or sample system rotation. Intensity or ellipsometric data vs. sample rotation angle is also useful in determining the orientation of in-plane $n_x$ and $n_y$ refractive indices with respect to "P" and "S" directions, as well as to determine the direction of $n_z$ with respect to a normal to an alignment surface of the sample system under investigation. Further, if there is minimal difference between the effect of the in-plane ($n_x$*t) and ($n_y$*t) on a beam of electromagnetic radiation there will be few "wiggles" on a plot of anisotropic intensity(s), (ie. Jones Matrix components tpp, tss, tps, tsp) or ellipsometric ratios thereof, as a function of wavelength, and if there is a relatively large difference between the effect of the ($n_x$*t) and ($n_y$*t) on a beam of electromagnetic radiation there will be many "wiggles" on a plot of intensity or ellipsometric data as a function of, for instance, wavelength. Where plots as a function of angle-of-incidence are observed, out-of-plane differences in refractive indices can be estimated, (ie. differences between ($n_z$*t) and either ($n_x$*t) or ($n_y$*t), by observation of "wiggles" in intensity or ellipsometric, (ie. Jones Matrix components tpp, tss, tps, tsp or ratios thereof), data plotted as a function of said near-normal angles-of-incidence. Generally, it has been found beneficial to use the information so gleened to determine how to orient linear "P"-plane polarization direction of the beam of electromagnetic radiation with respect to the direction of the "in-plane" indices of refraction, ($n_x$) and ($n_y$) of a sample system. If few "wiggles" are observed in the identified plots as functions of wavelength and/or near-normal angles-of-incidence, it is has often been found best to orient said linearly polarized beam so that its P-Plane locus bisects the directions of the "in-plane" indices of refraction, ($n_x$) and ($n_y$) in following steps of the present invention method; and if many "wiggles" are observed, it is often best to orient said linearly polarized beam's "P"-plane so that it is oriented essentially along a direction of one of the "in-plane" indices of refraction, ($n_x$) and ($n_y$) in said following steps of the present invention method. Hence, the present invention method of determining values for anisotropic refractive indices $(n_x)$, $(n_y)$ and $(n_z)$ in, respectively, "x", "y" and "z" directions in a sample system can further comprise a preliminary qualitative step of obtaining data selected from the group consisting of:

transmission anisotropic intensity data;
transmission anisotropic ellipsometric data;
reflection anisotropic intensity data; and
reflection anisotropic ellipsometric data;

as a function of a selection from the group consisting of:

angle-of-incidence; and
wavelength;

and observing said data for the presence of "wiggles". Based upon said observation one then orients said sample system as described by a selection from the group consisting of:

1. so said linearly polarized beam locus bisects the directions of the "in-plane" indices of refraction, $(n_x)$ and $(n_y)$;
2. so said linearly polarized beam locus essentially aligns with the direction of one of the "in-plane" indices of refraction, $(n_x)$ and $(n_y)$.

FIG. 10 is included to demonstrate how the "wiggles" alluded to can appear in real ellipsometric PSI ($\psi$) data as a function of angle-of-incidence. The actual data shown is PSI ($\psi$) for a $TiO_2$ crystal, as a function of near-normal angle-of-incidence It is further to be appreciated that once the values for $(\Delta n_{xy})$, $(\Delta n_{xz})$ and $(\Delta n_{yz})$, and absolute values for all $(n_x)$, $(n_y)$ and $(n_z)$ and the directions (x), (y) and (z) thereof with respect to the alignment surface, are determined, an optional additional step is to obtain a multi-dimensional data set and re-evaluate all said values simultaneously to verify accuracy, and to provide dispersion information not acquired in steps where spectroscopic data was not utilized. Said additional step is much like what conventional ellipsometric methods utilize, but with the benefit of having very good, previously determined starting values for $(\Delta n_{xy})$, $(\Delta n_{xz})$ and $(\Delta n_{yz})$, and for absolute values for all $(n_x)$, $(n_y)$ and $(n_z)$, and for the directions (x), (y) and (z) thereof with respect to the alignment surface, being available.

It is again generally pointed out that the present invention has determined the fact that where it is desired to determine differences in in-plane, (ie. $\Delta n_{xy}$), refractive indices, then electromagnetic radiation should be directed along the direction of the out-of-plane refractive index $(n_z)$ and transmission data should be acquired and utilized in regression procedures. Where out-of-plane differences between refractive indices (ie. $\Delta n_{xz}$ and $(\Delta n_{yz})$), is/are to be determined, then electromagnetic radiation of at least one wavelength should be utilized and directed along near-normal angles-of-incidence around a normal to a sample system reference surface, and either transmission or reflection data acquired and utilized in regression procedures. And, where it is desired to evaluate absolute value(s) of one or more refractive indices (ie. $(n_x)$, $(n_y)$ and $(n_z)$), in an anisotropic sample system, then reflectance, and/or transmission data obtained utilizing angles-of-incidence at and/or around the Brewster angle are preferably utilized. Refinements in practicing the present invention include orienting an ellipsometer electromagnetic beam plane of incidence with, or between in-plane, (ie. $(n_x)$, $(n_y)$), indices of refraction during the obtaining of data at near normal angles-of-incidence, and correcting for sample system backside reflections when obtaining reflectance data at near Brewster angles-of-incidence.

The present invention will be better understood by reference to the Detailed Description Section of this Disclosure, in conjunction with the Drawings.

SUMMARY OF THE INVENTION

An objective and/or purpose of the present invention is to provide a method of evaluating anisotropic sample system indices of refraction $(n_x)$, $(n_y)$ and $(n_z)$ and orientations thereof with respect to an alignment surface of said sample system, said method comprising a sequence of steps which require that only relatively simple one-dimensional data sets be acquired.

Another objective and/or purpose of the present invention is to provide a method of evaluating anisotropic sample system indices of refraction $(n_x)$, $(n_y)$ and $(n_z)$ and orientations thereof with respect to an alignment surface of said sample system, which method utilizes data sets acquired with electromagnetic beams oriented at near-normal incidence to an alignment surface of said sample system so that the difference between the in-plane $(\Delta n_{xy})$ indices of refraction and the Euler angle orientations of said in-plane orthogonal $(n_x)$ $(n_y)$ indices of refraction are determined, and so the difference between at least one out-of-plane combination of indices of refraction selected from the group consisting of:

$(\Delta n_{xz})$;

and $(\Delta n_{yz})$;

can be determined.

Yet another objective and/or purpose of the present invention is to provide a method of evaluating absolute values for anisotropic sample system indices of refraction $(n_x)$, $(n_y)$ and $(n_z)$, and orientations thereof with respect to an alignment surface of a sample system; which method utilizes data obtained at near Brewster angle angles-of-incidence, in combination with previously obtained values for $(\Delta n_{xy})$ and $(\Delta n_{xz})$ or $(\Delta n_{yz})$, which were evaluated utilizing data sets obtained at near normal angles-of-incidence.

Another, general objective and/or purpose of the present invention is to particularly point out that ellipsometric or intensity transmission and/or reflection data obtained by investigation of a sample system utilizing angles-of-incidence which are near-normal to a surface of said sample system, are predominately sensitive to differences between orthogonal indices of refraction; while ellipsometric or intensity transmission or reflection data obtained by investigation of a sample system utilizing angles-of-incidence which are near the Brewster angle of a sample system, (where backside reflections are appropriately accounted for), are predominately sensitive to absolute values of in-plane refractive indices $(n_x)$ or $(n_y)$; and further, that spectroscopic transmission ellipsometric or intensity data obtained with an incident beam of electromagnetic radiation oriented along the direction of an out-of-plane refractive index $(n_z)$ is identified as particularly sensitive to $(\Delta n_{xy})$, and transmission or reflection ellipsometric or intensity data obtained with an incident beam of electromagnetic radiation oriented at numerous near normal angles-of-incidence is identified as particularly sensitive to $(\Delta n_{xz})$ or $(\Delta n_{yz})$.

Other objectives and/or purposes of the present invention will become apparent by reference to the Specification.

BRIEF DESCRIPTION OF THE DRAWINGS

FIG. 3 demonstrates a preferred present invention method.

DETAILED DESCRIPTION

Figure 1:
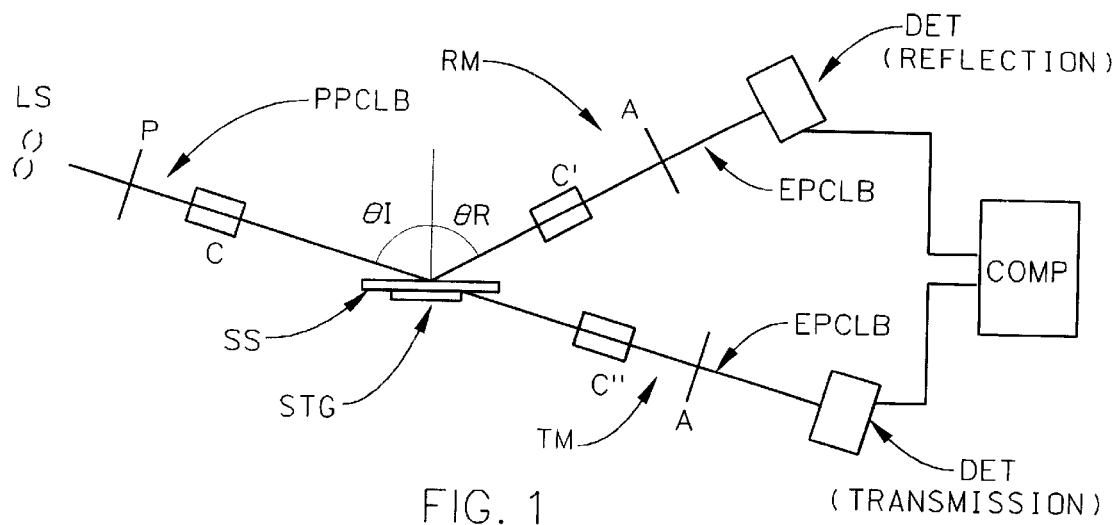
FIG. 1 demonstrates an ellipsometer/polarimeter system with both reflection and transmission detector capability.

Turning now to FIG. 1 for demonstrative insight, a typical ellipsometer/polarimeter system is shown. Shown are:

1. a source of a beam of electromagnetic radiation (LS);
2. a polarizer (P);
3. a stage for supporting a sample system (STG);
4. an analyzer (A);
5. a reflection detector (DET-REFLECTION);
6. a transmission detector (DET-TRANSMISSION);
7. a compensator ((C), (C') (C")) at some point between said polarizer (P) and analyzer (A); and
8. indication of a computational means, (COMP) which can be a computer system of sufficient capacity and capability.

(Note: it should be understood that at least one of the compensators shown can represent modulation element(s) in a phase-modulation ellipsometer system).

In particular note that an incident beam (PPCLB) of electromagnetic radiation is caused to impinge on a sample system (SS) at an angle-of-incidence of ($\theta_I$) and indication of a reflection mode (RM) beam (EPCLB) oriented at an angle of ($\theta_R$) and a transmission mode (TM) beam (EPCLB) are also present. The angle ($\theta_R$) of reflected (RM) beam (EPCLB) beam and the angle ($\theta_I$) of the incident beam PPCLB are equal, and the transmission mode (TM) beam proceeds at an angle determined by Snell's Law as applied to the sample system (SS) and surrounding ambient. It is to be appreciated that where the angle-of-incidence is near normal, (eg. within +/−45 degrees to a normal to a surface of a sample system ), and transmission data is obtained and utilized, values of ($\Delta n_{xy}$), ($\Delta n_{xz}$) and ($\Delta n_{yz}$), can be ascertained therefrom, whereas such values are typically completely obscured where reflection ellipsometry is practiced with an electromagnetic beam directed at a sample system surface at a near Brewster Angle angle-of-incidence, which for semiconductors is approximately seventy-five (75) degrees. Where a near-Brewster angle of incidence is utilized, sensitivity to absolute values of indices of refraction ($n_x$), ($n_y$) and ($n_z$) obtain. As described the Disclosure of the Invention Section of this Specification, the present invention methodology works because of this "separation-out" determination of ($\Delta n_{xy}$), ($\Delta n_{xz}$) and/or ($\Delta n_{yz}$) by use of data obtained utilizing "near normal" angles of incidence.

Figure 2:
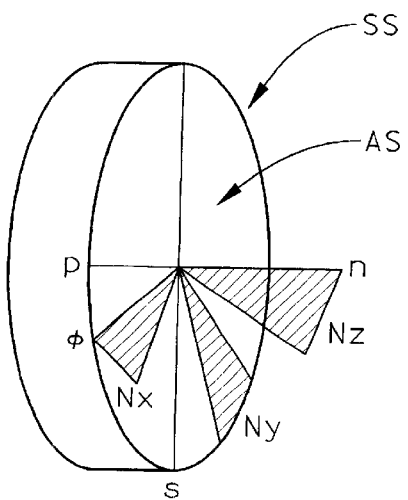
FIG. 2 shows a sample system with anisotropic sample system indices of refraction $(n_x)$, $(n_y)$ and $(n_z)$, with variable orientations thereof with respect to an alignment surface of said sample system.

FIG. 2 demonstrates a Sample System (SS) with anisotropic in-plane orthogonal refractive indices indicated as ($N_x$) ($N_y$) and out-of-plane anisotropic refractive index indicated as ($N_z$), all oriented with respect to an alignment surface (AS). It is said anisotropic refractive indices ($N_x$), ($N_y$) and ($N_z$), as well as their orientations with respect to the Alignment Surface (AS) of the Sample System (SS) which the present invention methodology serves to evaluate. The normal "n" to the surface (AS) is indicated, and represents the direction of the transmitted beam at normal incidence, and the "P" and "S" directions are shown for electromagnetic radiation normal to the surface (AS). It is noted that a plane-of-incidence includes the normal "n" and the "P" directions. To arrive at the directions of the anisotropic refractive indices ($N_x$), ($N_y$) and ($N_z$) a PHI ($\phi$) angle rotation of about the Sample System (SS) Normal "n", and a THETA ($\theta$) angle rotation about a surface contained in-plane, (as demonstrated by $THETA_I$ ($\theta_I$), in FIG. 1 are indicated.

FIG. 3 demonstrates, in diagram form, a preferred method of the present invention. Said demonstrated methodology assumes the presence of an ellipsometer or the like system with a sample system (SS) present therein, and picks-up with the determination of the precise orientation of the third index of refraction ($n_z$) which projects essentially perpendicular to said alignment surface thereof. Once said orientation is known, the method proceeds to causing a spectroscopic beam of electromagnetic radiation originating from said source of a beam of electromagnetic radiation, (which spectroscopic beam of electromagnetic radiation is comprised of a plurality of wavelengths for which said sample system is essentially transparent), to preferably become essentially linearly polarized and approach said alignment surface of said sample system along a locus which is essentially co-incident with the orientation of the third index of refraction ($n_z$) which projects essentially perpendicular to said alignment surface, partially transmit through said sample system and enter said transmission detector to the end that a one-dimensional data set as a function of wavelength is acquired. This is followed by applying said computational means which is programmed with a mathematical model for said sample system to results and/or data acquired in previous steps to the end that a value for the difference between the in-plane ($\Delta n_{xy}$) indices of refraction and the Euler angle orientations of said essentially in-plane orthogonal ($n_x$) ($n_y$) indices of refraction are determined.

The method continues by causing a beam of electromagnetic radiation originating from said source of a beam of electromagnetic radiation, which beam of electromagnetic radiation is comprised of at least one wavelength for which said sample system is essentially transparent, to preferably become essentially linearly polarized and approach said alignment surface of said sample system along a plurality of near normal angles-of-incidence to said sample system alignment surface, partially transmit through said sample system and enter said transmission detector to the end that a one dimensional data set as a function of angle-of-incidence is acquired. Then, again, said computational means, which is programmed with a mathematical model for said sample system is applied to results and/or data acquired in previous steps to the end that a value for the difference between at least one out-of-plane combination of indices of refraction selected from the group consisting of:

$(\Delta n_{xz})$;

and $(\Delta n_{yz})$;

and is determined. (It is noted that reflection detector acquired data could also be utilized in this step in place of, or in addition to the transmission data indicated).

Next, a beam of electromagnetic radiation is caused to originate from said source of a beam of electromagnetic radiation, which beam of electromagnetic radiation is comprised of at least one wavelength, to preferably become essentially linearly polarized and approach said alignment surface of said sample system along a plurality of angles-of-incidence at near the Brewster condition to said sample system alignment surface, partially reflect from said alignment surface of said sample system and enter said reflection detector to the end that data as a function of angle-of-incidence is acquired. Then said computational means which is programmed with a mathematical model for said sample system is applied to results and/or data acquired in previous steps to the end that an absolute value for at least one index of refraction selected from the group consisting of:

$(n_x)$;

$(n_y)$;

$(n_z)$;

is directly determined, and, if desired and/or required, from previously determined values for $(\Delta n_{xy})$, $(\Delta n_{xz})$ and $(\Delta n_{yz})$, determining absolute values for $(n_x)$, $(n_y)$ or $(n_z)$ not directly evaluated. (It is noted that transmission data could also be utilized in this step in place of, or in addition to the reflection data indicated).

Optionally further steps are performed by causing a beam of spectroscopic electromagnetic radiation originating from said source of a beam of electromagnetic radiation to preferably become essentially linearly polarized and approach said alignment surface of said sample system along a plurality of angles-of-incidence to said sample system alignment surface, partially transmit through or reflect from said sample system and enter said transmission or reflection detector to the end that data as a function of wavelength and angle-of-incidence is acquired, and then applying said computational means which is programmed with a mathematical model for said sample system to results and/or data acquired in previous steps to the end that dispersion data for at least one index of refraction selected from the group consisting of:

$(n_x)$;

$(n_y)$;

$(n_z)$;

is determined.

It is specifically disclosed that the computational means can be any computer system with sufficient data storage and computational capability.

To provide better insight as to the basis of various steps in the present invention, FIGS. 4–9 are presented. Generally said Figures show Diagonal Jones Matrix PSI ($\Psi$) and DELTA ($\Delta$) values for demonstrative sample systems. First, it should be recalled that a transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

represents mathematically how a sample system (SS) affects a polarized electromagnetic beam, with Epi and Esi orthogonal components, which is caused to transmissively interact therewith. Further, an ellipsometer/polarimeter system can return an on-diagonal ratio:

$$(Tpp/Tss) = \text{Tan}\left(\psi_{\frac{pp}{ss}}\right)\left(e^{i\Delta\frac{pp}{ss}}\right);$$

and off-diagonal ratios:

$$(Tsp/Tss) = \text{Tan}\left(\psi_{\frac{sp}{ss}}\right)\left(e^{i\Delta\frac{sp}{ss}}\right);$$

$$(Tps/Tss) = \text{Tan}\left(\psi_{\frac{ps}{ss}}\right)\left(e^{i\Delta\frac{ps}{ss}}\right);$$

$$(Tsp/Tpp) = \text{Tan}\left(\psi_{\frac{sp}{pp}}\right)\left(e^{i\Delta\frac{sp}{pp}}\right);$$

$$(Tps/Tpp) = \text{Tan}\left(\psi_{\frac{ps}{pp}}\right)\left(e^{i\Delta\frac{ps}{pp}}\right);$$

as a function of a selection from the group consisting of:

angle-of-incidence;

wavelength; and sample system rotation about a normal to said alignment surface.

A similar Jones Matrix can be formed for Reflection:

$$\begin{bmatrix} Epo \\ Eso \end{bmatrix} = \begin{bmatrix} Rpp & Rsp \\ Rps & Rss \end{bmatrix} \begin{bmatrix} Epi \\ Esi \end{bmatrix}$$

and similar on-diagonal and off-diagonal ratios can be formed, wherein the "T" is replaced with "R".

Figure 4:
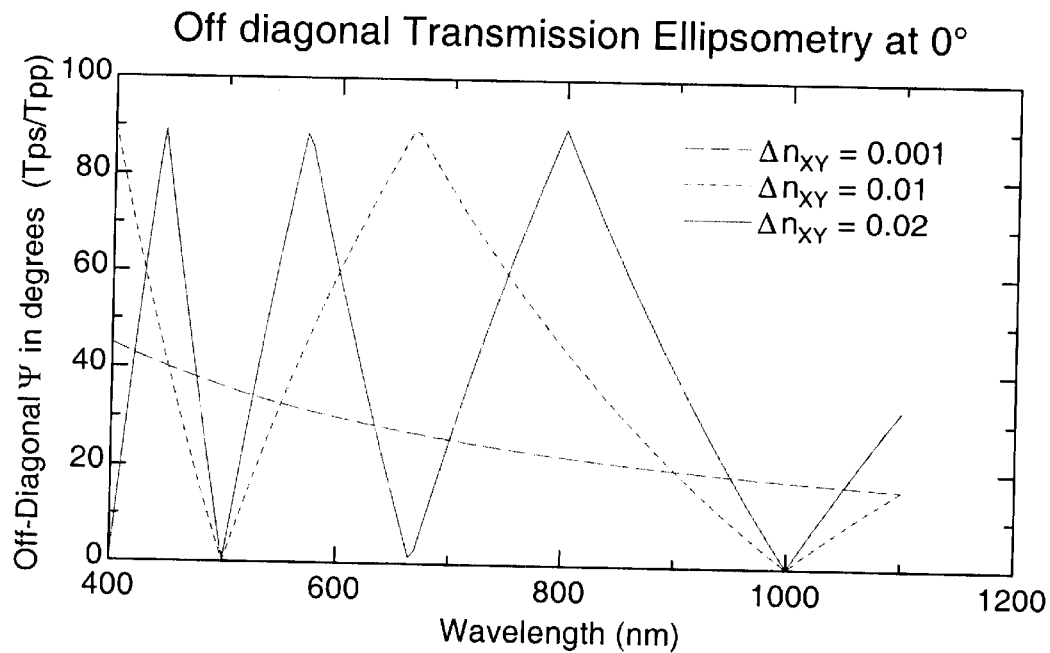
FIG. 4 shows generated off-diagonal PSI ($\psi$) values vs. wavelength for a sample system of constant thickness, but wherein the ($\Delta n_{xy}$) values are 0.001, 0.01 and 0.02.

FIG. 4 shows generated off-diagonal PSI ($\Psi$) values vs. wavelength for a sample system of constant thickness of 0.1 MM, wherein sample system in-plane PHI ($\phi$), (see FIG. 2 for identification of PHI ($\phi$)), is set at a constant forty-five (45) degrees and where the ($\Delta n_{xy}$) values are varied through 0.001, 0.01 and 0.02. The plotted data corresponds to the case where the ellipsometer beam of electromagnetic radiation is directed along the direction of ($n_z$) of the sample system, (which is ideally perpendicular to the surface of the sample system), and transmits through said sample system before being detected, (as described in the Step 2 in FIG. 3), so that effects of ($n_z$) are eliminated. Note that as the sample system ($\Delta n_{xy}$) values increase, the off-diagonal PSI plot changes. This demonstrates a measurable PSI data variation, which the present method utilizes to determine ($\Delta n_{xy}$).

FIG. 5, 6a, 6b and 6c should be observed in conjunction with FIG. 4, and serve to provide better insight to how off-diagonal PSI values for a sample system vary as a function of PHI ($\phi$).

Figure 5:
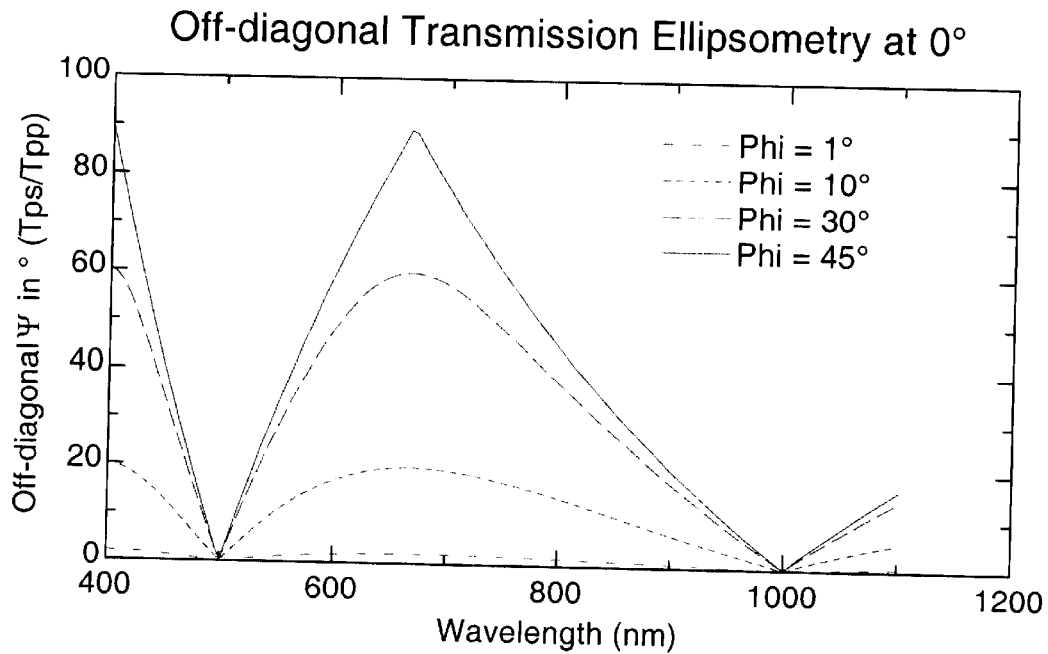
FIG. 5 shows a plot of off-diagonal transmission PSI ($\psi$) vs. wavelength for ellipsometric beam plane positions of sample system in-plane angle PHI ($\phi$) between an orientation of essentially one (1) degree, through forty-five (45) degrees.
Figure 6A:
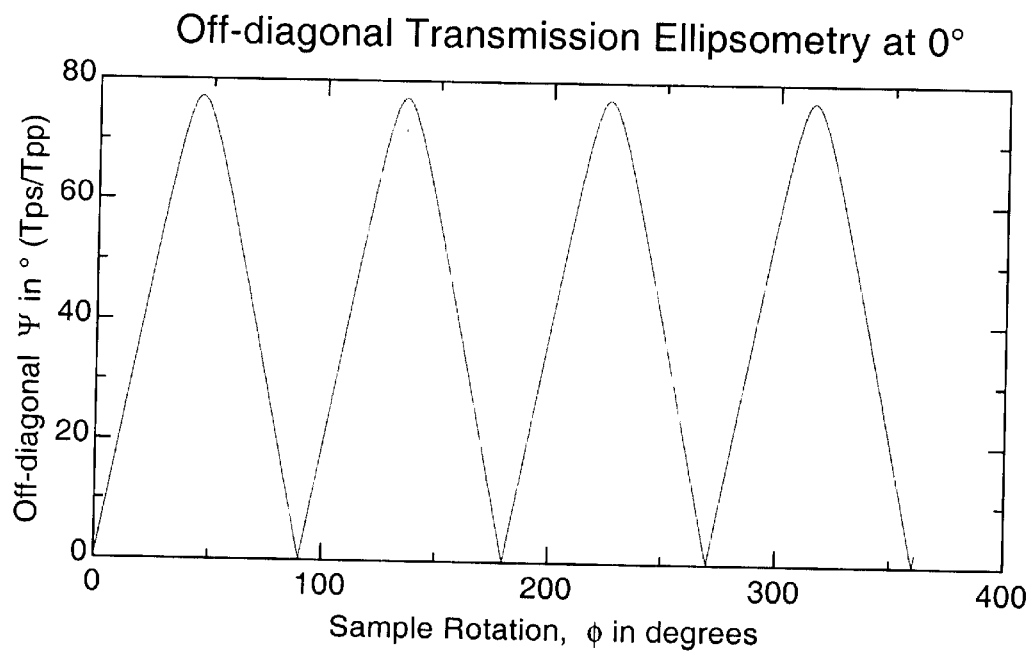
FIG. 6a shows off-diagonal PSI ($\psi$) vs. sample system rotation PHI ($\phi$), for a single wavelength of 700 NM.
Figure 6B:
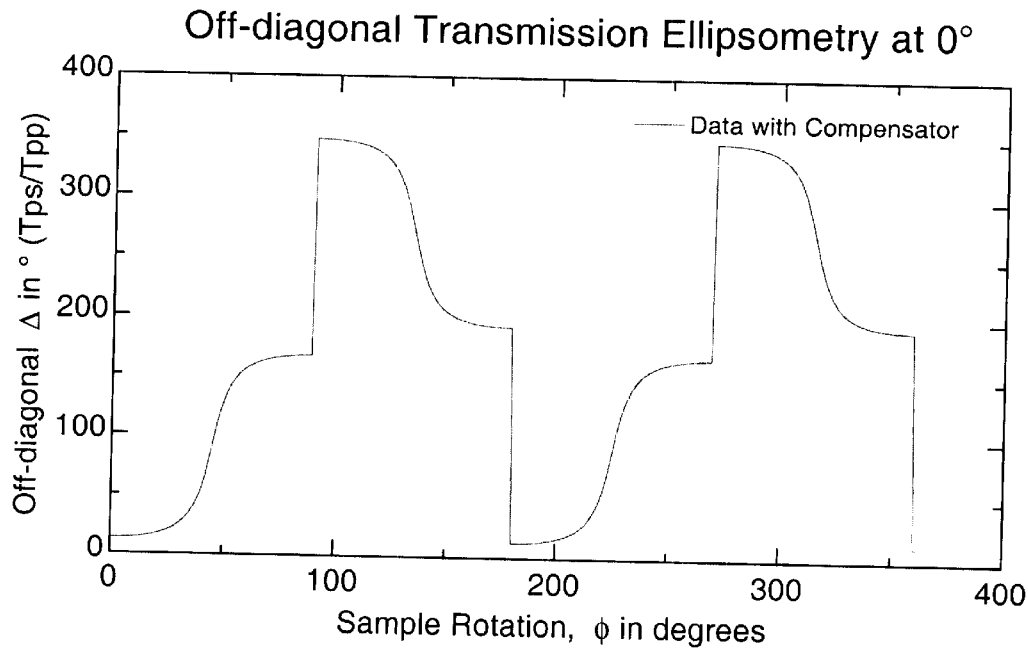
FIG. 6b shows off-diagonal DELTA ($\Delta$) vs. sample system rotation PHI ($\phi$), for a single wavelength of 700 NM, when a compensator is placed in the ellipsometer.
Figure 6C:
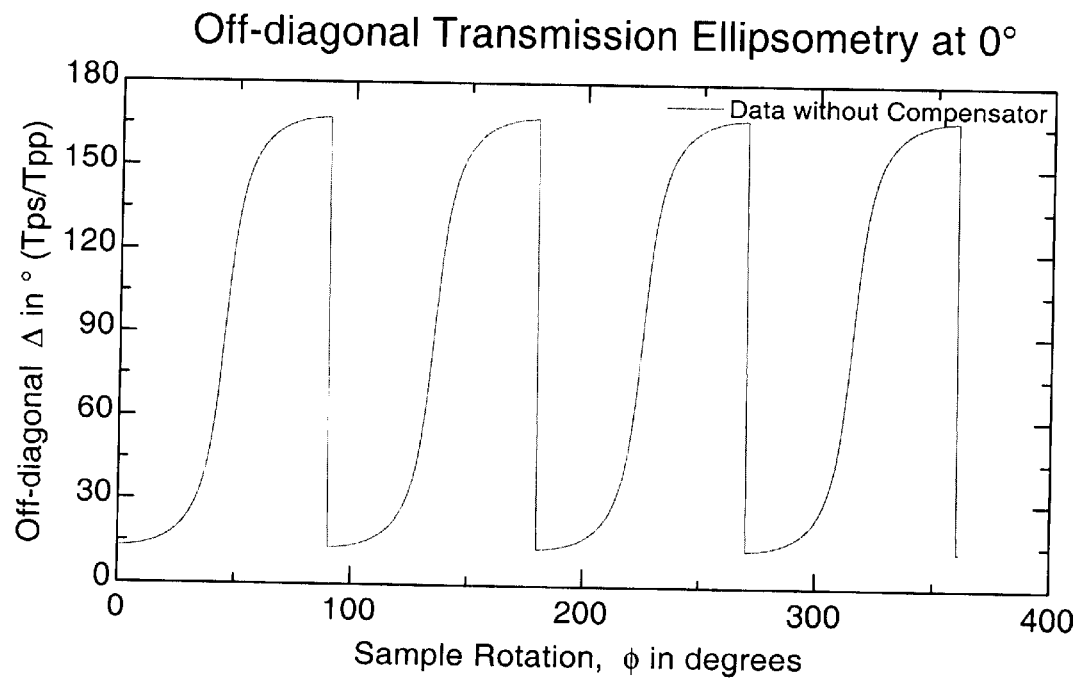
FIG. 6c shows off-diagonal DELTA ($\Delta$) vs. sample system rotation PHI ($\phi$), for a single wavelength of 700 NM, when no compensator is present in the ellipsometer.

FIG. 5 shows generated off-diagonal PSI (Ψ) values vs. wavelength for a sample system of constant thickness of 0.1 MM, wherein ($\Delta n_{xy}$) is set to 0.01, wherein PHI (φ), (see FIG. 2), is varied through 1.0, 10, 30 and 45 Degrees. FIG. 5 shows that as PHI (φ) varies the off-diagonal PSI values, as a function of wavelength, vary. FIG. 6a shows a plot of sample system off-diagonal PSI (Ψ) values vs. sample system rotation about the direction of ($n_z$), (ie. as a function of angle PHI (φ)). FIG. 6a shows that said off-diagonal PSI (Ψ) data alone is not sufficient to distinguish between a PHI (φ) angle range of 0.0 to 45 degrees and a PHI (φ) angle range of 45 to 90 degrees. FIG. 6c shows that rotating analyzer ellipsometer system, without a compensator present therein, obtained sample system off-diagonal DELTA (Δ) data, as a function of PHI (φ), is likewise insufficient to distinguish between a PHI (φ) angle range of 0.0 to 90 degrees and a PHI (φ) angle range of 90 to 180 degrees. FIG. 6b, however, shows that for rotating analyzer ellipsometer system, with a compensator, (see FIG. 1 "C", "iC'" "C"), present therein, obtained sample system off-diagonal DELTA (Δ) data, as a function of PHI (φ), provides DELTA (Δ) data which is unambiguous over a range of PHI (φ) of from 0.0 to 180 degrees.

Figure 7:
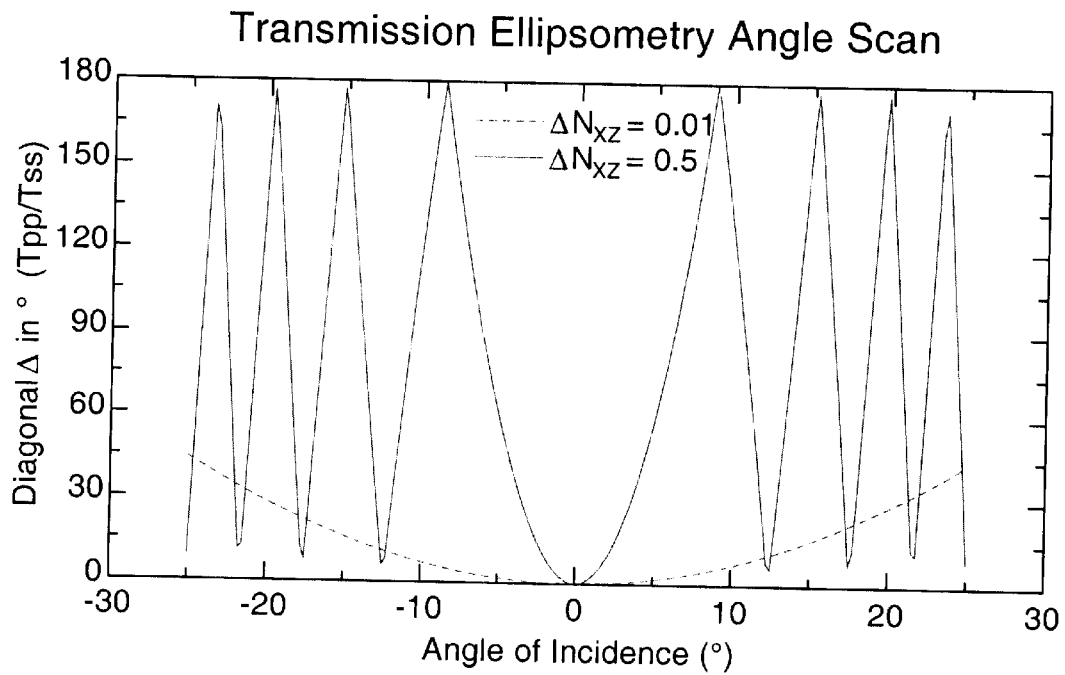
FIG. 7 shows on-diagonal DELTA ($\Delta$) vs. near normal Angle-of-Incidence for a single wavelength of 700 NM, for two ($\Delta n_{xz}$) values for a sample system.

FIG. 7 shows sample system on-diagonal near-normal transmission DELTA (Δ) data, as a function of near normal Angle-of-Incidence, at a constant wavelength of 700 NM, and for two values of ($\Delta n_{xz}$) namely, 0.01 and 0.2. The sample system is assumed to have a thickness of 0.1 MM, and the plane of the ellipsometric beam of electromagnetic radiation is assumed to include the direction of ($n_z$), which is assumed to be perpendicular to the sample system surface. Note that as the ($\Delta n_{xz}$) value changes, the plot in FIG. 7 changes. It is this measurable change which allows finding the ($\Delta n_{xz}$) vales in Step 3 of FIG. 3.

Figure 8:
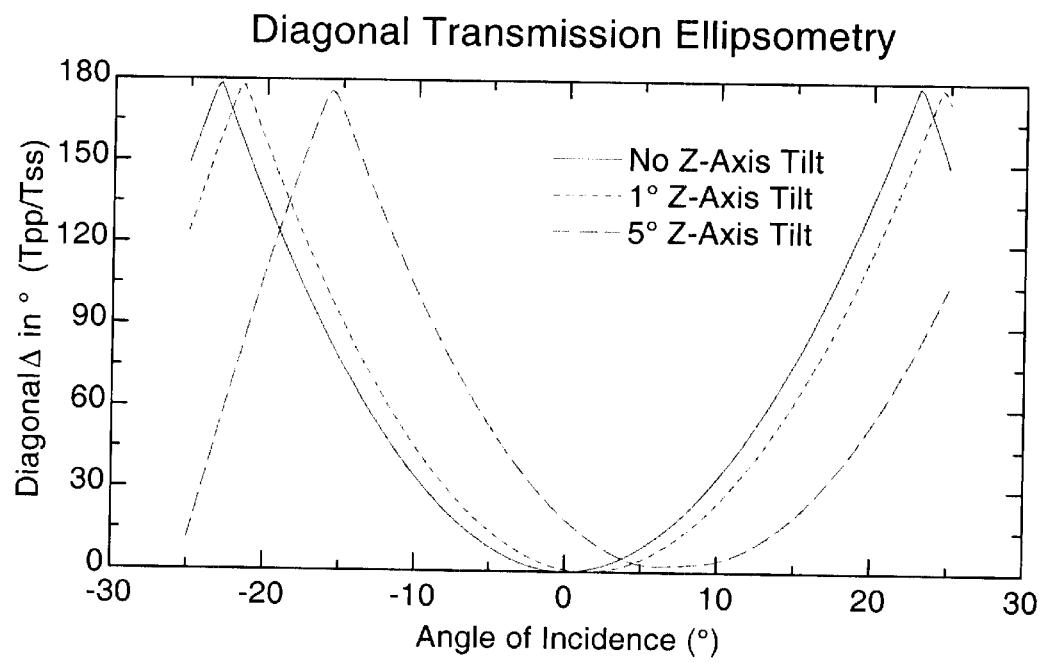
FIG. 8 shows on-diagonal DELTA ($\Delta$) vs. near normal Angle-of-Incidence for $n_z$ directed perpendicularly to the surface of the sample system, and offset therefrom by one (1) and five (5) degrees in the plane of the incident ellipsometer beam.

FIG. 8 shows a sample system on-diagonal near-normal transmission DELTA (Δ) data, as a function of near-normal Angle-of-Incidence for a constant 700 NM wavelength. The sample system is assumed to have a thickness of 0.1 MM, and the plane of the ellipsometric beam of electromagnetic radiation is assumed to include the direction of ($n_z$). The ellipsometric electromagnetic beam plane of incidence is varied between a perpendicular to the sample system surface, and 1.0 and 5.0 degrees tilt away from said normal. This data shows that once an ellipsometric electromagnetic beam plane of incidence is determined, that varying the electromagnetic beam near normal Angle-of-Incidence allows identification of the projected direction of ($n_z$) in said ellipsometric electromagnetic beam plane of incidence.

Figure 9A:
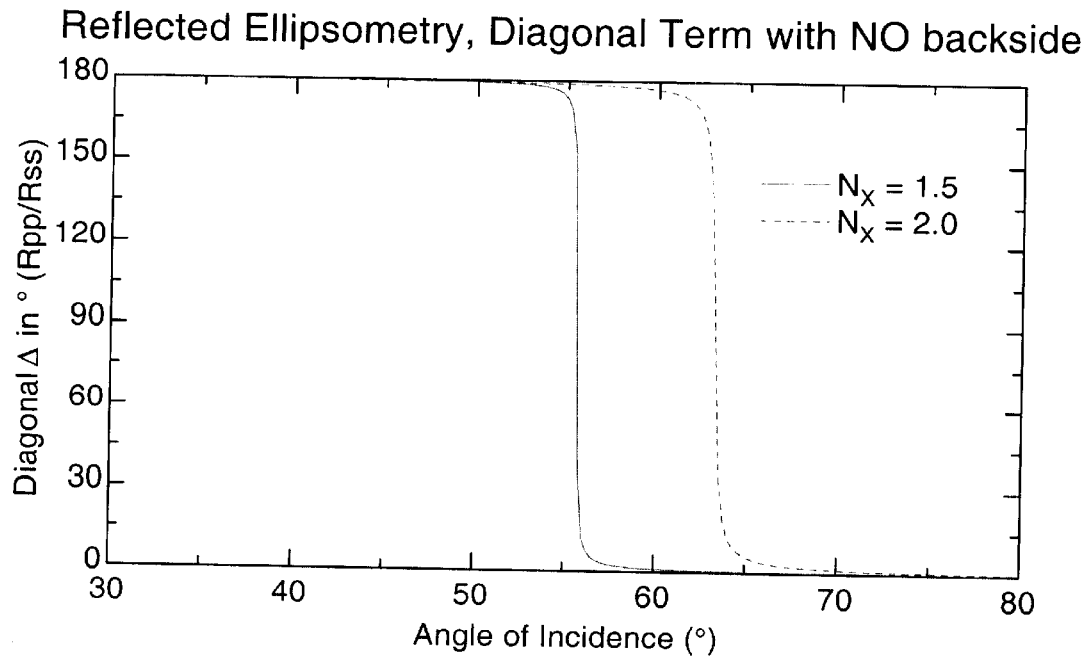
FIGS. 9a and 9b show on-diagonal DELTA ($\Delta$) vs. near Brewster Angle Angle-of-Incidence, for cases wherein there are no backside reflections, and for the case wherein backside reflections are present, respectively.
Figure 9B:
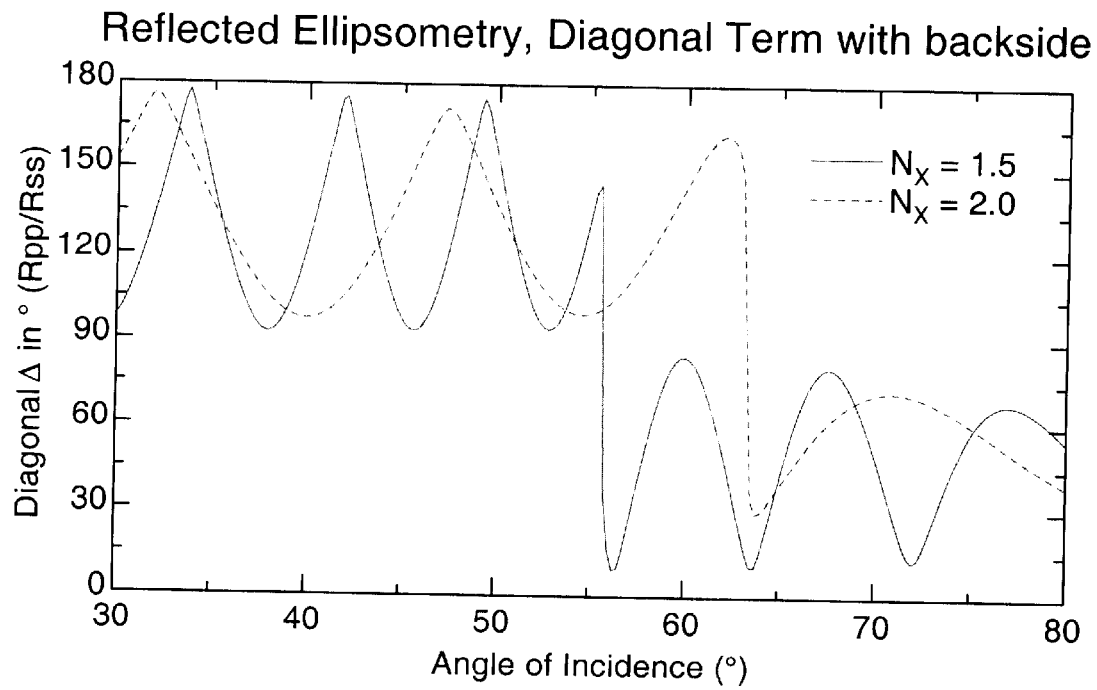

FIGS. 9a and 9b provide insight to practice of Step 4 in FIG. 3, wherein an absolute value for at least one of the in-plane, ($n_x$) and ($n_y$), indices of refraction, is determined. FIGS. 9a and 9b both show plots of sample system on-diagonal Reflection DELTA (Δ), as a function of near-Brewster Angle, (eg. see ($\Theta_I$) in FIG. 1), Angle-of-Incidence. The sample system is investigated with a constant wavelength of 700 NM, and the sample system is again assumed to have a thickness of 0.1 MM. Plots are shown for the case where back-side reflections from the sample system occur, (FIG. 9b), and where such back-side reflections are suppressed (FIG. 9a), by, for instance, roughening the back side of the sample system prior to obtaining data. The important point exemplified is that where back-side reflections are present, they must be taken into account in the mathematical model of the sample system. It is also noted that as the index of refraction of a sample system increases, the Brewster angle increases, and that where anisotropic indices of refraction are present, the various effects caused by ($n_x$), ($n_y$) and ($n_z$) in a beam of electromagnetic radiation interacting therewith at specified angles thereof with respect to said ($n_x$), ($n_y$) and ($n_z$), must be accounted for in the mathematical model.

Figure 10:
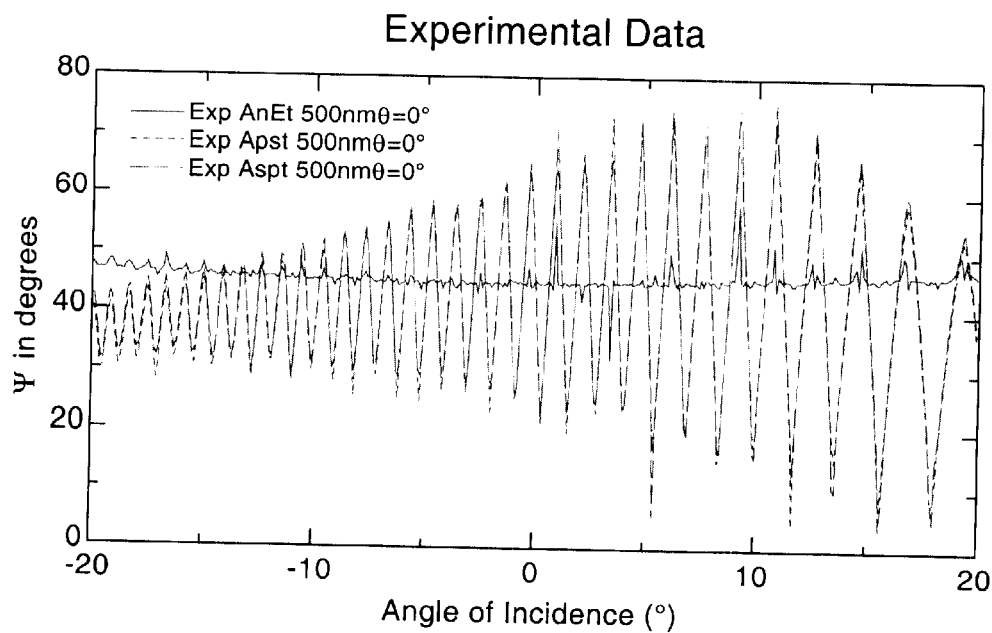
FIG. 10 shows "wiggles" in real ellipsometric PSI ($\psi$) data as a function of angle-of-incidence, obtained from investigation of a $TiO_2$ crystal.

As discussed in the Disclosure of the Invention Section of this Specification, FIG. 10 is included to demonstrate how the "wiggles" alluded to can appear in real ellipsometric PSI (Ψ) data as. a function of near-normal angle-of-incidence. FIG. 10 shows off-diagonal PSI (Ψ) data obtained from investigation of a $TiO_2$ crystal.

It is again noted that the present invention is enabled by the fact the ellipsometric or intensity transmission data, obtained by investigation of a sample system utilizing angles-of-incidence which are near-normal to a surface of said sample system, are sensitive to differences between orthogonal indices of refraction; while ellipsometric or intensity transmission or reflection data obtained by investigation of a sample system utilizing angles-of-incidence which are near the Brewster angle of a sample system, (where backside reflections are appropriately accounted for), are predominately sensitive to absolute values of in-plane refractive indices ($n_x$) or ($n_y$). Further, spectroscopic transmission ellipsometric or intensity data obtained with an incident beam of electromagnetic radiation oriented along the direction of an out-of-plane refractive index is identified as particularly sensitive to ($\Delta n_{xy}$), and transmission ellipsometric or intensity data obtained with an incident beam of electromagnetic radiation oriented at numerous near normal angles-of-incidence is identified as particularly sensitive to ($\Delta n_{xz}$) or ($\Delta n_{yz}$).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of determining values for anisotropic refractive indices $n_x$, $n_y$ and $n_z$ in orthogonally related directions in a sample system comprising, in any functional order, the steps of:

a) providing a system selected from the group consisting of:
   an ellipsometer;
   a polarimeter; and
   a spectrophotometer;

said system being comprised of at least selections 1, 3, 5, 6, and 9, from the group consisting of:

1) a source of a beam of electromagnetic radiation;

2) a polarizer;

3) a stage for supporting a sample system;

4) an analyzer;

5) a reflection detector;

6) a transmission detector;

7) a compensator at some point between said polarizer and analyzer;

8) a modulation element at some point between said polarizer and analyzer;

9) a computational means which is programmed with a mathematical model for said sample system, said mathematical model serving to relate indices of refraction, thickness and optical axis direction over a range of at least one member of the group consisting of:
   wavelength;

"P" plane angle-of-incidence of an investigating polarized beam of electromagnetic radiation to an alignment surface of said material system; and sample system rotation angle about a perpendicular to an alignment surface thereof;

which computational means includes a routine for fitting numbers to said mathematical model parameters in view of experimental data;

said method further comprising practicing steps b, c, d, and e in any functional order, said steps b, c, d, and e being:

b) providing, and determining the thickness of, a sample system having two essentially in-plane $(n_x)$ $(n_y)$ orthogonal indices of refraction in an alignment surface thereof and a third $(n_z)$ index of refraction which projects essentially perpendicular to said alignment surface;

c) determining a range of wavelengths for which said sample system is essentially transparent;

d) placing said sample system on the stage for supporting a sample system so that said alignment surface thereof is accessible by a beam of electromagnetic radiation originating from said source of a beam of electromagnetic radiation;

e) determining the precise orientation of the third index of refraction which projects essentially perpendicular to said alignment surface thereof;

said method further comprising:

f) causing a spectroscopic beam of electromagnetic radiation originating from said source of a beam of electromagnetic radiation, which spectroscopic beam of electromagnetic radiation is comprised of a plurality of wavelengths for which said sample system is essentially transparent, to approach said alignment surface of said sample system along a locus which is essentially co-incident with the orientation of the third index of refraction which projects essentially perpendicular to said alignment surface, at least partially transmit through said sample system and enter said transmission detector to the end that a one-dimensional data set as a function of wavelength is acquired;

g) applying said computational means which is programmed with a mathematical model for said sample system to said step f results in view of results from practice of previous steps, to the end that a value for the difference between the in-plane $(\Delta n_{xy})$ indices of refraction and the Euler angle orientations of said essentially in-plane orthogonal $(n_x)$ $(n_y)$ indices of refraction are determined;

h) causing a beam of electromagnetic radiation originating from said source of a beam of electromagnetic radiation, which beam of electromagnetic radiation is comprised of at least one wavelength, to approach said alignment surface of said sample system along a plurality of near normal angles-of-incidence to said sample system alignment surface, interact with said sample system and enter at least one selection from the group consisting of:
said reflection detector; and
said transmission detector;

to the end that a one dimensional data set as a function of angle-of-incidence is acquired;

i) applying said computational means which is programmed with a mathematical model for said sample system to said step h results in view of results from practice of previous steps to the end that a value for the difference between at least one out-of-plane combination of indices of refraction selected from the group consisting of:

$(\Delta n_{xz})$;

and $(\Delta n_{yx})$;

and
is determined;

j) causing a beam of electromagnetic radiation originating from said source of a beam of electromagnetic radiation, which beam of electromagnetic radiation is comprised of at least one wavelength, to approach said alignment surface of said sample system along a plurality of angles-of-incidence at near the Brewster condition to said sample system alignment surface, interact with said sample system and enter at least one selection from the group consisting of:
said reflection detector; and
said transmission detector;

to the end that data as a function of angle-of-incidence is acquired;

k) applying said computational means which is programmed with a mathematical model for said sample system to said step j results in view of results from practice of previous steps to the end that an absolute value for at least one index of refraction selected from the group consisting of:

$(n_x)$;

$(n_y)$;

$(n_z)$;

is directly determined;

said method optionally further comprising steps 1 and m, said steps 1 and m being:

1) causing a beam of spectroscopic electromagnetic radiation originating from said source of a beam of electromagnetic radiation to approach said alignment surface of said sample system along a plurality of angles-of-incidence to said sample system alignment surface, and enter at least one selection from the group consisting of:
said transmission detector; and
said reflection detector;

to the end that data as a function of wavelength and angle-of-incidence is acquired; and m) applying said computational means which is programmed with a mathematical model for said sample system to the end that dispersion data for at least one index of refraction selected from the group consisting of:

$(n_x)$;

$(n_y)$;

$(n_z)$;

is determined.

2. A method of determining values for anisotropic refractive indices $n_x$, $n_y$ and $n_z$ as in claim 1, in which at least the step k determination of at least one index of refraction selected from the group consisting of:

($n_x$);

($n_y$);

($n_z$);

includes accounting for sample system back-side reflections by appropriately allocating intensity calculation into coherent and incoherent components.

3. A method of determining values for anisotropic refractive indices $n_x$, $n_y$ and $n_z$ as in claim 1, in which the step a provision of a system includes providing a polarizer and an analyzer and a compensator at some point between said polarizer and analyzer; and in which the step g determination of a value for the difference between the in-plane ($\Delta n_{xy}$) indices of refraction and the Euler angle orientations of said in-plane orthogonal ($n_x$) ($n_y$) indices of refraction involves obtaining and utilizing data obtained with said compensator in position in said system.

4. A method of determining values for anisotropic refractive indices $n_x$, $n_y$ and $n_z$ as in claim 3, wherein said compensator is present in a compensator system which provides at least one adjustable means for controlling a phase angle between orthogonal components in a polarized beam of light, which adjustable means for controlling a phase angle, in use, allows sequentially setting a plurality of phase angles between orthogonal components in a polarized beam of light which is caused by said system to interact with a sample system, such that in use said phase angle can be set sequentially through a plurality of settings while data is obtained by said means for monitoring a polarization state in said polarized beam of light at at least two selected settings of said at least one adjustable means for controlling an phase angle.

5. A method of determining values for anisotropic refractive indices $n_x$, $n_y$ and $n_z$ as in claim 1, in which the step h plurality of near-normal angles-of-incidence to said sample system alignment surface are in a range of about negative forty-five (−45) to positive forty-five (+45) degrees.

6. A method of determining values for anisotropic refractive indices $n_x$, $n_y$ and $n_z$ as in claim 1, in which the step e determination of the precise orientation of the third index of refraction which projects essentially perpendicular to said alignment surface thereof involves at least one selection from the group consisting of I and II, said I and II being:

a) by optical techniques determining the magnitude(s) of at least one member of the group consisting of:
real;
imaginary; and
a combination of real and imaginary components;

for at least one ratio of components of a material system representing transmission Jones matrix as a function of at least one member of the group consisting of:
wavelength;
"P" plane angle-of-incidence of an investigating polarized beam of electromagnetic radiation to an alignment surface of said material system; and
sample system rotation angle about a perpendicular to the alignment surface thereof;

said at least one ratio of material system representing transmission Jones matrix components being selected from the group consisting of:
on-diagonal ratio ($Tpp/Tss$);

and off-diagonal ratios ($Tsp/Tss$);
($Tps/Tss$);
($Tsp/Tpp$);
($Tps/Tpp$);

where Tpp, Tss, Tps and Tsp are the components of a two dimensional material system representing transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

which material system representing transmission Jones matrix describes the change in polarization state between said incident and transmitted portions of said beam of electromagnetic radiation;

b) providing a mathematical model of said material system comprising at least one deviation angle calibration parameter which represents a non-coincidence of said optical axis with a desired locus with respect to said alignment surface, said mathematical model serving to relate indices of refraction, thickness and optical axis direction over a range of at least one member of the group consisting of:
wavelength;
"P" plane angle-of-incidence of an investigating polarized beam of electromagnetic radiation to an alignment surface of said material system; and
sample system rotation angle about a perpendicular to the alignment surface thereof;

c) performing a regression procedure of said mathematical model onto said magnitude of at least one member of the group consisting of:
real;
imaginary; and
a combination of real and imaginary components;

of at least one step a selected ratio of material system representing transmission Jones matrix components as a function of at least one member of the group consisting of:
wavelength;
"P" plane angle-of-incidence of an investigating polarized beam of electromagnetic radiation to an alignment surface of said material system; and
sample system rotation angle about a perpendicular to the alignment surface thereof;

such that said at least one deviation angle calibration parameter is evaluated; and a) by ellipsometric techniques effectively obtaining a plot of a sample system PSI ($\Psi$) vs sample system rotation angle about a perpendicular to a surface of said sample system, and therefrom determining the in-plane angle at which the plane of incidence of said ellipsometric beam of electromagnetic radiation includes the direction of ($n_x$) or ($n_y$), by noting where minima and/or maxima occur in said effective plot; and b) with the plane of incidence of said ellipsometric beam of electromagnetic radiation positioned as determined in step a, so as to include the direction of ($n_x$) or ($n_y$), effectively obtaining a plot of a DELTA ($\Delta$) vs ellipsometric electromagnetic beam angle-of-incidence about a normal to the surface of said sample system, and therefrom determining a minima and/or maxima symetry point in said effective plot, said minima and/or maxima symetry point being identifying of the projected direction of ($n_z$) in said ellipsometric electromagnetic beam plane of incidence;

such that sample system rotation angle PHI ($\phi$), about a perpendicular to the surface of said sample system, at which the ellipsometric beam of radiation plane of incidence includes the direction of ($n_z$), and the angle of said projected direction of ($n_z$) with respect to the normal to the sample system surface, are determined.

7. A method of determining values for anisotropic refractive indices $n_x$, $n_y$ and $n_z$ as in claim 1, which further comprises a qualitative step of, prior to step a, obtaining data selected from the group consisting of:
transmission anisotropic intensity data;
transmission anisotropic ellipsometric data;
reflection anisotropic intensity data; and
reflection anisotropic ellipsometric data;
as a function of a selection from the group consisting of:
angle-of-incidence; and
wavelength;
and observing said data for the presence of "wiggles";
and based thereupon orienting said sample system as described by a selection from the group consisting of:

1) so said linearly polarized beam locus bisects the directions of the "in-plane" indices of refraction, ($n_x$) and ($n_y$);
2) so said linearly polarized beam locus essentially aligns with the direction of one of the "in-plane" indices of refraction, ($n_x$) and ($n_y$).

8. A method of determining values for anisotropic refractive indices $n_x$, $n_y$ and $n_z$ as in claim 7, in which the first selection from the group consisting of;

1) so said linearly polarized beam locus bisects the directions of the "in-plane" indices of refraction, ($n_x$) and ($n_y$);
2) so said linearly polarized beam locus essentially aligns with the direction of one of the "in-plane" indices of refraction, ($n_x$) and ($n_y$);
is adopted if few wiggles appear in said obtained data, and in which said second selection from said group consisting of:
1) so said linearly polarized beam locus bisects the directions of the "in-plane" indices of refraction, ($n_x$) and ($n_y$);
2) so said linearly polarized beam locus essentially aligns with the direction of one of the "in-plane" indices of refraction, ($n_x$) and ($n_y$);
is adopted if numerous wiggles appear in said data.

9. A method of determining values for anisotropic refractive indices $n_x$, $n_y$ and $n_z$ in orthogonally related directions in a sample system comprising, in any functional order, the steps of:

a) providing a system selected from the group consisting of:
an ellipsometer;
a polarimeter; and
a spectrophotometer;
said system being comprised of at least selections 1, 3, 5, 6, and 9, from the group consisting of:
1) a source of a beam of electromagnetic radiation;
2) a polarizer;
3) a stage for supporting a sample system;
4) an analyzer;
5) a reflection detector;
6) a transmission detector;
7) a compensator at some point between said polarizer and analyzer;
8) a modulation element at some point between said polarizer and analyzer; and
9) a computational means which is programmed with a mathematical model for said sample system, said mathematical model serving to relate indices of refraction, thickness and optical axis direction over a range of at least one member of the group consisting of:
wavelength;
"P" plane angle-of-incidence of an investigating polarized beam of electromagnetic radiation to an alignment surface of said material system; and
sample system rotation angle about a perpendicular to an alignment surface thereof;
which computational means includes a routine for fitting numbers to said mathematical model parameters in view of experimental data;
said method further comprising practicing steps b, c, d, and e in any functional order, said steps b, c, d, and e being:

b) providing, and determining the thickness of, a sample system having two essentially in-plane ($n_x$) ($n_y$) orthogonal indices of refraction in an alignment surface thereof and a third ($n_z$) index of refraction which projects essentially perpendicular to said alignment surface;

c) determining a range of wavelengths for which said sample system is essentially transparent;

d) placing said sample system on the stage for supporting a sample system so that said alignment surface thereof is accessible by a beam of electromagnetic radiation originating from said source of a beam of electromagnetic radiation;

e) determining the precise orientation of the third index of refraction which projects essentially perpendicular to said alignment surface thereof;

said method further comprising step groups:
f and g; and
h and i;
said step groups being performed at least one time each in either order, said steps f, g, h and i being:

f) causing a spectroscopic beam of electromagnetic radiation originating from said source of a beam of electromagnetic radiation, to approach said alignment surface of said sample system along a locus which is essentially co-incident with the orientation of the third index of refraction which projects essentially perpendicular to said alignment surface, interact with said sample system and monitoring the results by at least one selection from the group consisting of:
said transmission detector; and
said reflection detector;
to the end that data as a function of wavelength is acquired;

g) applying said computational means which is programmed with a mathematical model for said sample system, in view of results of practice of previous steps, to the end that a value for the difference between the in-plane ($\Delta n_{xy}$) indices of refraction and the Euler angle orientations of said essentially in-plane orthogonal ($n_x$) ($n_y$) indices of refraction are determined;

h) causing a beam of electromagnetic radiation originating from said source of a beam of electromagnetic radiation, which beam of electromagnetic radiation is comprised of at least one wavelength, to approach said alignment surface of said sample system along a plurality of near-normal angles-of-incidence to said sample system alignment surface, interact with said sample system and monitoring the results by at least one selection from the group consisting of:
said transmission detector; and
said reflection detector;
to the end that data as a function of angle-of-incidence is acquired;

i) applying said computational means which is programmed with a mathematical model for said sample system, in view of results of practice of previous steps, to the end that a value for the difference between at least one out-of-plane combination of indices of refraction selected from the group consisting of:

$(\Delta n_{xz})$;

and $(\Delta n_{yz})$;

and
is determined;
said method further comprising:

j) causing a beam of electromagnetic radiation originating from said source of a beam of electromagnetic radiation, which beam of electromagnetic radiation is comprised of at least one wavelength, to approach said alignment surface of said sample system along a plurality of angles-of-incidence at near the Brewster condition to said sample system alignment surface, interact said sample system and monitoring the results by at least one selection from the group consisting of:
said transmission detector; and
said reflection detector;
to the end that data as a function of angle-of-incidence is acquired;

k) applying said computational means which is programmed with a mathematical model for said sample system, in view of results of practice of previous steps, to the end that an absolute value for at least one index of refraction selected from the group consisting of:

$(n_x)$;

$(n_y)$;

$(n_z)$;

is directly determined;
said method optionally further comprising steps l and m, said steps l and m being:

l) causing a beam of spectroscopic electromagnetic radiation originating from said source of a beam of electromagnetic radiation to approach said alignment surface of said sample system along a plurality of angles-of-incidence to said sample system alignment surface, interact said sample system and monitoring the results by at least one selection from the group consisting of:
said transmission detector; and
said reflection detector;
to the end that data as a function of wavelength and angle-of-incidence is acquired; and m) applying said computational means which is programmed with a mathematical model for said sample system, in view of results of practice of previous steps, to the end that dispersion data for at least one index of refraction selected from the group consisting of:

$(n_x)$;

$(n_y)$;

$(n_z)$;

is determined.

10. A method of determining values for anisotropic refractive indices $n_x$, $n_y$ and $n_z$ as in claim 9, in which at least the step k determination of at least one index of refraction selected from the group consisting of:

$(n_x)$;

$(n_y)$;

$(n_z)$;

includes accounting for sample system back-side reflections by appropriately allocating intensity calculation into coherent and incoherent components.

11. A method of determining values for anisotropic refractive indices $n_x$, $n_y$ and $n_z$ as in claim 9, in which the step a provision of a system includes providing a polarizer and an analyzer, and a compensator at some point between said polarizer and analyzer; and in which the step g determination of a value for the difference between the in-plane ($\Delta n_{xy}$) indices of refraction and the Euler angle orientations of said in-plane orthogonal ($n_x$) ($n_y$) indices of refraction involves obtaining and utilizing data obtained with said polarizer and compensator in position in said system.

12. A method of determining values for anisotropic refractive indices $n_x$, $n_y$ and $n_z$ as in claim 11, wherein said compensator is present in a compensator system which provides at least one adjustable means for controlling a phase angle between orthogonal components in a polarized beam of light, which adjustable means for controlling a phase angle, in use, allows sequentially setting a plurality of phase angles between orthogonal components in a polarized beam of light which is caused by said system to interact with a sample system, such that in use said phase angle can be set sequentially through a plurality of settings while data is obtained by said means for monitoring a polarization state in said polarized beam of light at at least two selected settings of said at least one adjustable means for controlling an phase angle.

13. A method of determining values for anisotropic refractive indices $n_x$, $n_y$ and $n_z$ as in claim 9, in which the step h plurality of near-normal angles-of-incidence to said sample system alignment surface are in a range of about negative forty-five (−45) to positive forty-five (+45) degrees.

14. A method of determining values for anisotropic refractive indices $n_x$, $n_y$ and $n_z$ as in claim 9, in which the step e determination of the precise orientation of the third index of refraction which projects essentially perpendicular to said alignment surface thereof involves at least one selection from the group consisting of I and II, said I and II being:

I a) by optical techniques determining the magnitude(s) of at least one member of the group consisting of:
real;
imaginary; and
a combination of real and imaginary components;
for at least one ratio of components of a material system representing transmission Jones matrix as a function of at least one member of the group consisting of:

wavelength;

"P" plane angle-of-incidence of an investigating polarized beam of electromagnetic radiation to an alignment surface of said material system; and sample system rotation angle about a perpendicular to the alignment surface thereof;

said at least one ratio of material system representing transmission Jones matrix components being selected from the group consisting of:

on-diagonal ratio (Tpp/Tss);

and off-diagonal ratios (Tsp/Tss);

(Tps/Tss);

(Tsp/Tpp);

(Tps/Tpp);

where Tpp, Tss, Tps and Tsp are the components of a two dimensional material system representing transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

which material system representing transmission Jones matrix describes the change in polarization state between said incident and transmitted portions of said beam of electromagnetic radiation;

b) providing a mathematical model of said material system comprising at least one deviation angle calibration parameter which represents a non-coincidence of said optical axis with a desired locus with respect to said alignment surface, said mathematical model serving to relate indices of refraction, thickness and optical axis direction over a range of at least one member of the group consisting of:

wavelength;

"P" plane angle-of-incidence of an investigating polarized beam of electromagnetic radiation to an alignment surface of said material system; and sample system rotation angle about a perpendicular to the alignment surface thereof;

c) performing a regression procedure of said mathematical model onto said magnitude of at least one member of the group consisting of:

real;

imaginary; and a combination of real and imaginary components;

of at least one step a selected ratio of material system representing transmission Jones matrix components as a function of at least one member of the group consisting of:

wavelength;

"P" plane angle-of-incidence of an investigating polarized beam of electromagnetic radiation to an alignment surface of said material system; and sample system rotation angle about a perpendicular to the alignment surface thereof;

such that said at least one deviation angle calibration parameter is evaluated; and

II a) by ellipsometric techniques effectively obtaining a plot of a sample system PSI ($\Psi$) vs sample system rotation angle about a perpendicular to a surface of said sample system, and therefrom determining the in-plane angle at which the plane of incidence of said ellipsometric beam of electromagnetic radiation includes the direction of ($n_x$) or ($n_y$), by noting where minima and/or maxima occur in said effective plot; and b) with the plane of incidence of said ellipsometric beam of electromagnetic radiation positioned as determined in step a., so as to include the direction of ($n_x$) or ($n_y$), effectively obtaining a plot of a DELTA ($\Delta$) vs ellipsometric electromagnetic beam angle-of-incidence about a normal to the surface of said sample system, and therefrom determining a minima and/or maxima symetry point in said effective plot, said minima and/or maxima symetry point being identifying of the projected direction of ($n_z$) in said ellipsometric electromagnetic beam plane of incidence;

such that sample system rotation angle PHI ($\phi$), about a perpendicular to the surface of said sample system, at which the ellipsometric beam of radiation plane of incidence includes the direction of ($n_z$), and the angle of said projected direction of ($n_z$) with respect to the normal to the sample system surface, are determined.

15. A method of determining values for anisotropic refractive indices $n_x$, $n_y$ and $n_z$ as in claim 9, which further comprises a qualitative step of obtaining data selected from the group consisting of:

transmission anisotropic intensity data;

transmission anisotropic ellipsometric data;

reflection anisotropic intensity data; and reflection anisotropic ellipsometric data;

as a function of a selection from the group consisting of:

angle-of-incidence; and wavelength;

and observing said data for the presence of "wiggles";

and based thereupon orienting said sample system as described by a selection from the group consisting of:

1) so said linearly polarized beam locus bisects the directions of the "in-plane" indices of refraction, ($n_x$) and ($n_y$);

2) so said linearly polarized beam locus essentially aligns with the direction of one of the "in-plane" indices of refraction, ($n_x$) and ($n_y$).

16. A method of determining values for anisotropic refractive indices $n_x$, $n_y$ and $n_z$ in, respectively, "x", "y" and "z" directions in a sample system comprising as in claim 15, in which the first selection from the group consisting of;

1) so said linearly polarized beam locus bisects the directions of the "in-plane" indices of refraction, ($n_x$) and ($n_y$);

2) so said linearly polarized beam locus essentially aligns with the direction of one of the "in-plane" indices of refraction, ($n_x$) and ($n_y$);

is adopted if few wiggles appear in said obtained data, and in which said second selection from said group consisting of:

1) so said linearly polarized beam locus bisects the directions of the "in-plane" indices of refraction, ($n_x$) and ($n_y$);

2) so said linearly polarized beam locus essentially aligns with the direction of one of the "in-plane" indices of refraction, ($n_x$) and ($n_y$);

is adopted if numerous wiggles appear in said data.

17. A method of determining values for anisotropic refractive indices $n_x$, $n_y$ and $n_z$ in orthogonally related directions in a sample system comprising, in any functional order, the steps of:

a) providing a system selected from the group consisting of:
   an ellipsometer;
   a polarimeter; and
   a spectrophotometer;

said system being comprised of at least selections 1, 2, 3, 4, 5, 6, and 9, from the group consisting of:

1) a source of a beam of electromagnetic radiation;
2) a polarizer;
3) a stage for supporting a sample system;
4) an analyzer;
5) a reflection detector;
6) a transmission detector;
7) a compensator at some point between said polarizer and analyzer;
8) a modulation element at some point between said polarizer and analyzer; and
9) a computational means which is programmed with a mathematical model for said sample system, said mathematical model serving to relate indices of refraction, thickness and optical axis direction over a range of at least one member of the group consisting of:
   wavelength;
   "P" plane angle-of-incidence of an investigating polarized beam of electromagnetic radiation to an alignment surface of said material system; and
   sample system rotation angle about a perpendicular to an alignment surface thereof;

which computational means includes a square error reducing routine for fitting numbers to said mathematical model parameters in view of experimental data;

said method further comprising practicing steps b, c, and d in any functional order, said steps b, c, and d being:

b) providing, and determining the thickness of, a sample system having two essentially in-plane ($n_x$) ($n_y$) orthogonal indices of refraction in an alignment surface thereof and a third ($n_z$) index of refraction which projects essentially perpendicular to said alignment surface;

c) determining a range of wavelengths for which said sample system is essentially transparent;

d) placing said sample system on the stage for supporting a sample system so that said alignment surface thereof is accessible by a beam of electromagnetic radiation originating from said source of a beam of electromagnetic radiation;

said method further comprising step groups:

e and f; and g and h; said step groups being performed at least one time each in any functional order, said steps e, f, g, and h being:

e) causing a beam of electromagnetic radiation originating from said source of a beam of electromagnetic radiation, which beam of electromagnetic radiation is comprised of wavelength(s) for which said sample system is essentially transparent, to pass through said polarizer and become essentially linearly polarized and approach said alignment surface of said sample system, and monitoring the results by at least one selection from the group consisting of:
   said transmission detector; and
   said reflection detector;

while at least two selections from the group consisting of:
   angle-of-incidence;
   wavelength; and
   sample system rotation about a normal to said alignment surface;

are varied, to the end that data is acquired;

f) applying said computational means which is programmed with a mathematical model for said sample system, in view of results of practice of previous steps, to the end that, simultaneously, the precise orientation of the third index of refraction with respect to the alignment surface of said sample system, and the difference between the in-plane ($\Delta n_{xy}$) indices of refraction and the Euler angle orientations of said essentially in-plane orthogonal ($n_x$) ($n_y$) indices of refraction are simultaneously determined;

g) causing a beam of electromagnetic radiation originating from said source of a beam of electromagnetic radiation, to pass through said polarizer and approach said alignment surface of said sample system along a plurality of near normal angles-of-incidence to said sample system alignment surface, interact with said sample system and monitoring the results by at least one selection from the group consisting of:
   said transmission detector; and
   said reflection detector;

to the end that data as a function of angle-of-incidence is acquired;

h) applying said computational means which is programmed with a mathematical model for said sample system, in view of results of practice of previous steps, to the end that a value for the difference between at least one out-of-plane combination of indices of refraction selected from the group consisting of:

$$(\Delta n_{xz});$$

and $$(\Delta n_{yz});$$

and is determined;

said method further comprising:

i) causing a beam of electromagnetic radiation originating from said source of a beam of electromagnetic radiation, which beam of electromagnetic radiation is comprised of at least one wavelength, to pass through said polarizer and approach said alignment surface of said sample system along a plurality of angles-of-incidence at near the Brewster condition to said sample system alignment surface, interact said sample system and monitoring the results by at least one selection from the group consisting of:
   said transmission detector; and
   said reflection detector;

to the end that data as a function of angle-of-incidence is acquired;

j) applying said computational means which is programmed with a mathematical model for said sample system, in view of results of practice of previous steps, to the end that an absolute value for at least one index of refraction selected from the group consisting of:

$(n_x)$;

$(n_y)$;

$(n_z)$;

is directly determined;

said method optionally further comprising steps k and l, said steps k and l being:

k) causing a beam of spectroscopic electromagnetic radiation originating from said source of a beam of electromagnetic radiation to pass through said polarizer and approach said alignment surface of said sample system along a plurality of angles-of-incidence to said sample system alignment surface, interact with said sample system and monitoring the results by at least one selection from the group consisting of:
said transmission detector; and
said reflection detector;
to the end that data as a function of wavelength and angle-of-incidence is acquired;

l) applying said computational means which is programmed with a mathematical model for said sample system, in view of results of practice of previous steps, to the end that dispersion data for at least one index of refraction selected from the group consisting of:

$(n_x)$;

$(n_y)$;

$(n_z)$;

is determined.

18. A method of determining values for anisotropic refractive indices $n_x$, $n_y$ and $n_z$ as in claim 17, in which at least the step j determination of at least one index of refraction selected from the group consisting of:

$(n_x)$;

$(n_y)$;

$(n_z)$;

includes accounting for sample system back-side reflections by appropriately allocating intensity calculation into coherent and incoherent components.

19. A method of determining values for anisotropic refractive indices $n_x$, $n_y$ and $n_z$ as in claim 17, in which the step a provision of a system includes providing a compensator at some point between said polarizer and analyzer; and in which the step f determination of a value for the difference between the in-plane ($\Delta n_{xy}$) indices of refraction and the Euler angle orientations of said in-plane orthogonal $(n_x)$ $(n_y)$ indices of refraction involves obtaining and utilizing data obtained with said compensator in position in said system.

20. A method of determining values for anisotropic refractive indices $n_x$, $n_y$ and $n_z$ as in claim 19, wherein said compensator is present in a compensator system which provides at least one adjustable means for controlling a phase angle between orthogonal components in a polarized beam of light, which adjustable means for controlling a phase angle, in use, allows sequentially setting a plurality of phase angles between orthogonal components in a polarized beam of light which is caused by said system to interact with a sample system, such that in use said phase angle can be set sequentially through a plurality of settings while data is obtained by said means for monitoring a polarization state in said polarized beam of light at at least two selected settings of said at least one adjustable means for controlling an phase angle.

21. A method of determining values for anisotropic refractive indices $n_x$, $n_y$ and $n_z$ as in claim 17, in which the step g plurality of near-normal angles-of-incidence to said sample system alignment surface are in a range of about negative forty-five (−45) to positive forty-five (+45) degrees.

22. A method of determining values for anisotropic refractive indices $n_x$, $n_y$ and $n_z$ as in claim 17, which further comprises a qualitative step of obtaining data selected from the group consisting of:
transmission anisotropic intensity data;
transmission anisotropic ellipsometric data;
reflection anisotropic intensity data; and
reflection anisotropic ellipsometric data;
as a function of a selection from the group consisting of:
angle-of-incidence; and
wavelength;
and observing said data for the presence of "wiggles";
and based thereupon orienting said sample system as described by a selection from the group consisting of:
1) so said linearly polarized beam locus bisects the directions of the "in-plane" indices of refraction, $(n_x)$ and $(n_y)$;
2) so said linearly polarized beam locus essentially aligns with the direction of one of the "in-plane" indices of refraction, $(n_x)$ and $(n_y)$.

23. A method of determining values for anisotropic refractive indices $n_x$, $n_y$ and $n_z$ as in claim 22, in which the first selection from the group consisting of;
1) so said linearly polarized beam locus bisects the directions of the "in-plane" indices of refraction, $(n_x)$ and $(n_y)$;
2) so said linearly polarized beam locus essentially aligns with the direction of one of the "in-plane" indices of refraction, $(n_x)$ and $(n_y)$;
is adopted if few wiggles appear in said obtained data, and in which said second selection from said group consisting of:
1) so said linearly polarized beam locus bisects the directions of the "in-plane" indices of refraction, $(n_x)$ and $(n_y)$;
2) so said linearly polarized beam locus essentially aligns with the direction of one of the "in-plane" indices of refraction, $(n_x)$ and $(n_y)$;
is adopted if numerous wiggles appear in said data.

24. A method of determining values for anisotropic refractive indices $n_x$, $n_y$ and $n_z$ as in claim 17, in which, prior to step f, preliminary determination of starting values for the precise orientation of the third index of refraction which projects essentially perpendicular to said alignment surface thereof involves practice of at least one selection from the group consisting of I and II, said I and II being:

I a) by optical techniques determining the magnitude(s) of at least one member of the group consisting of:
real;
imaginary; and
a combination of real and imaginary components;
for at least one ratio of components of a material system representing transmission Jones matrix as a function of at least one member of the group consisting of:

wavelength;
"P" plane angle-of-incidence of an investigating polarized beam of electromagnetic radiation to an alignment surface. of said material system; and
sample system rotation angle about a perpendicular to the alignment surface thereof;
said at least one ratio of material system representing transmission Jones matrix components being selected from the group consisting of:
on-diagonal ratio $(Tpp/Tss)$;

and off-diagonal ratios $(Tsp/Tss)$;
$(Tps/Tss)$;
$(Tsp/Tpp)$;
$(Tps/Tpp)$;

where Tpp, Tss, Tps and Tsp are the components of a two dimensional material system representing transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

which material system representing transmission Jones matrix describes the change in polarization state between said incident and transmitted portions of said beam of electromagnetic radiation;
b) providing a mathematical model of said material system comprising at least one deviation angle calibration parameter which represents a non-coincidence of said optical axis with a desired locus with respect to said alignment surface, said mathematical model serving to relate indices of refraction, thickness and optical axis direction over a range of at least one member of the group consisting of:
wavelength;
"P" plane angle-of-incidence of an investigating polarized beam of electromagnetic radiation to an alignment surface of said material system; and
sample system rotation angle about a perpendicular to the alignment surface thereof;
c) performing a regression procedure of said mathematical model onto said magnitude of at least one member of the group consisting of:
real;
imaginary; and
a combination of real and imaginary components;
of at least one step a selected ratio of material system representing transmission Jones matrix components as a function of at least one member of the group consisting of:
wavelength;
"P" plane angle-of-incidence of an investigating polarized beam of electromagnetic radiation to an alignment surface of said material system; and
sample system rotation angle about a perpendicular to the alignment surface thereof;
such that said at least one deviation angle calibration parameter is evaluated; and

II a) by ellipsometric techniques effectively obtaining a plot of a sample system PSI ($\Psi$) vs sample system rotation angle about a perpendicular to a surface of said sample system, and therefrom determining the in-plane angle at which the plane of incidence of said ellipsometric beam of electromagnetic radiation includes the direction of ($n_x$) or ($n_y$), by noting where minima and/or maxima occur in said effective plot; and
b) with the plane of incidence of said ellipsometric beam of electromagnetic radiation positioned as determined in step a, so as to include the direction of ($n_x$) or ($n_y$), effectively obtaining a plot of a DELTA ($\Delta$) vs ellipsometric electromagnetic beam angle-of-incidence about a normal to the surface of said sample system, and therefrom determining a minima and/or maxima symetry point in said effective plot, said minima and/or maxima symetry point being identifying of the projected direction of ($n_z$) in said ellipsometric electromagnetic beam plane of incidence;

such that sample system rotation angle PHI ($\phi$), about a perpendicular to the surface of said sample system, at which the ellipsometric beam of radiation plane of incidence includes the direction of ($n_z$), and the angle of said projected direction of ($n_z$) with respect to the normal to the sample system surface, are determined.

25. A method of determining values for anisotropic refractive indices $n_x$, $n_y$ and $n_z$ as in claim 5, in which the step h plurality of near-normal angles-of-incidence to said sample system alignment surface are within an extended range of from negative twenty (−20) to positive twenty (+20) degrees with respect to a normal to the alignment surface of a sample system.

26. A method of determining values for anisotropic refractive indices $n_x$, $n_y$ and $n_z$ as in claim 13, in which the step h plurality of near-normal angles-of-incidence to said sample system alignment surface are within an extended range of from negative twenty (−20) to positive twenty (+20) degrees with respect to a normal to the alignment surface of a sample system.

27. A method of determining values for anisotropic refractive indices $n_x$, $n_y$ and $n_z$ as in claim 21, in which the step g plurality of near-normal angles-of-incidence to said sample system alignment surface are within an extended range of from negative twenty (−20) to positive twenty (+20) degrees with respect to a normal to the alignment surface of a sample system.

* * * * *